United States Patent
Nakamura

(10) Patent No.: US 10,622,541 B2
(45) Date of Patent: Apr. 14, 2020

(54) ULTRASONIC DEVICE, ULTRASONIC MODULE, AND ULTRASONIC MEASUREMENT APPARATUS

(71) Applicant: Seiko Epson Corporation, Tokyo (JP)

(72) Inventor: Tomoaki Nakamura, Chino (JP)

(73) Assignee: Seiko Epson Corporation (JP)

( * ) Notice: Subject to any disclaimer, the term of this patent is extended or adjusted under 35 U.S.C. 154(b) by 528 days.

(21) Appl. No.: 15/444,720

(22) Filed: Feb. 28, 2017

(65) Prior Publication Data

US 2017/0263846 A1 Sep. 14, 2017

(30) Foreign Application Priority Data

Mar. 9, 2016 (JP) .................. 2016-045884

(51) Int. Cl.
| | |
|---|---|
| H01L 41/09 | (2006.01) |
| H01L 41/083 | (2006.01) |
| B06B 1/06 | (2006.01) |
| A61B 8/00 | (2006.01) |
| B06B 1/10 | (2006.01) |
| H01L 41/047 | (2006.01) |

(Continued)

(52) U.S. Cl.
CPC .......... *H01L 41/083* (2013.01); *A61B 8/4281* (2013.01); *A61B 8/4427* (2013.01); *A61B 8/4444* (2013.01); *A61B 8/4483* (2013.01); *B06B 1/06* (2013.01); *B06B 1/0688* (2013.01); *B06B 1/10* (2013.01); *H01L 41/0475* (2013.01); *H01L 41/0815* (2013.01); *H01L 41/0825* (2013.01); *G01S 7/52079* (2013.01)

(58) Field of Classification Search
USPC .................................. 310/322, 334
See application file for complete search history.

(56) References Cited

U.S. PATENT DOCUMENTS

| | | | |
|---|---|---|---|
| 2006/0142659 A1* | 6/2006 | Okazaki | ............... B06B 1/0622 600/459 |
| 2007/0282204 A1 | 12/2007 | Yamashita et al. | |
| 2013/0229893 A1 | 9/2013 | Shibamoto et al. | |

(Continued)

FOREIGN PATENT DOCUMENTS

| | | |
|---|---|---|
| JP | 2642068 B2 | 8/1997 |
| JP | 2008-011494 A | 1/2008 |

(Continued)

*Primary Examiner* — Thomas M Dougherty
(74) *Attorney, Agent, or Firm* — Harness, Dickey & Pierce, P.L.C.

(57) ABSTRACT

An ultrasonic device includes an ultrasonic transducer that has a vibration film and transmits an ultrasonic wave from a first surface side of the vibration film, an acoustic matching layer that is provided on the first surface side of the vibration film, and an acoustic lens that is provided on the acoustic matching layer on an opposite side to the vibration film, in which the acoustic matching layer is formed of even-numbered layers including a first layer and a second layer having acoustic impedance lower than acoustic impedance of each of the first layer and the acoustic lens, and the first layer and the second layer are disposed in this order toward the acoustic lens from the vibration film, and in which each of the first layer and the second layer has a thickness corresponding to an odd-numbered multiple of $\lambda/4$ with a wavelength of the ultrasonic wave as $\lambda$.

7 Claims, 12 Drawing Sheets

(51) Int. Cl.
*H01L 41/08* (2006.01)
*G01S 7/52* (2006.01)

(56) References Cited

U.S. PATENT DOCUMENTS

| | | | | |
|---|---|---|---|---|
| 2014/0221841 A1* | 8/2014 | Okuda | ............... | A61B 8/4444 |
| | | | | 600/459 |
| 2015/0141827 A1* | 5/2015 | Kiyose | ............... | A61B 8/4427 |
| | | | | 600/443 |
| 2015/0273526 A1 | 10/2015 | Tsuruno et al. | | |
| 2015/0305714 A1* | 10/2015 | Spigelmyer | .......... | A61B 8/4483 |
| | | | | 600/443 |

FOREIGN PATENT DOCUMENTS

| JP | 2012-114713 A | 6/2012 |
|---|---|---|
| JP | 2015-195351 A | 11/2015 |

* cited by examiner

ULTRASONIC DEVICE, ULTRASONIC MODULE, AND ULTRASONIC MEASUREMENT APPARATUS

BACKGROUND

1. Technical Field

The present invention relates to an ultrasonic device, an ultrasonic module, and an ultrasonic measurement apparatus.

2. Related Art

In the related art, there is a piezoelectric device including a vibration film and a piezoelectric element as a vibrator causing the vibration film to vibrate, provided on the vibration film (for example, JP-A-2015-195351). The piezoelectric device transmits an ultrasonic wave by driving the piezoelectric element and causing the vibration film to vibrate, and receives an ultrasonic wave by detecting vibration of the vibration film caused by the ultrasonic wave with the piezoelectric element.

The piezoelectric device disclosed in JP-A-2015-195351 further includes an acoustic matching layer provided on the vibration film, and an acoustic lens which is provided on the acoustic matching layer and has acoustic impedance similar to that of a living body as a measurement target. The piezoelectric device transmits and receives ultrasonic waves in a state in which the acoustic lens is brought into contact with a measurement target such as a living body. For example, an ultrasonic wave transmitted through driving of the piezoelectric element propagates through the acoustic matching layer and the acoustic lens, and is then output into a living body from a surface of the acoustic lens.

Here, as described above, in the configuration in which the acoustic matching layer and the acoustic lens are laminated, there is a case where some ultrasonic waves (hereinafter, also referred to as first waves) transmitted from the vibrator are output to a measurement target from the acoustic lens, and other ultrasonic waves are reflected at an interface between the acoustic matching layer and the acoustic lens. In this case, interface reflected waves which are reflected at the interface are reflected toward the acoustic lens side in the vibrator, and are output to the living body from the acoustic lens, and thus there is concern that a distance resolution may be reduced.

In other words, the interface reflected waves are delayed by the time corresponding to a thickness of the acoustic matching layer with respect to the first waves, and are then emitted to the measurement target. Thus, the first waves reflected from the measurement target and the interface reflected waves reflected from the measurement target are detected at different timings. In this case, there is a problem in that so-called tailing occurs in which not only a peak corresponding to the first waves but also a peak corresponding to the interface reflected waves is detected in a received signal which is output when the piezoelectric device receives the ultrasonic waves, and thus a distance resolution is reduced.

SUMMARY

An advantage of some aspects of the invention is to provide an ultrasonic device, an ultrasonic module, and an ultrasonic measurement apparatus, capable of improving a distance resolution.

An ultrasonic device according to an application example includes an ultrasonic transducer that has a vibration film and transmits an ultrasonic wave from a first surface side of the vibration film; an acoustic matching layer that is provided on the first surface side of the vibration film; and an acoustic lens that is provided on the acoustic matching layer on an opposite side to the vibration film, in which the acoustic matching layer is formed of even-numbered layers including a first layer and a second layer having acoustic impedance lower than acoustic impedance of each of the first layer and the acoustic lens, and the first layer and the second layer are disposed in this order toward the acoustic lens from the vibration film, and in which each of the first layer and the second layer has a thickness corresponding to an odd-numbered multiple of $\lambda/4$ with a wavelength of the ultrasonic wave as $\lambda$.

In this application example, the acoustic matching layer is formed of even-numbered layers such as the first layer and the second layer which are disposed in this order from the vibration film side. Each of the first layer and the second layer has a thickness corresponding to an odd-numbered multiple of $\lambda/4$ with a wavelength of the ultrasonic wave transmitted from the ultrasonic transducer as $\lambda$. The second layer has acoustic impedance lower than that of each of the first layer and the acoustic lens. In other words, in the application example, the acoustic matching layer is formed of the even-numbered layers, and the magnitude of the acoustic impedances of the respective layers adjacent to each other decreases from the vibration film toward the acoustic lens.

In this configuration, even if interface reflected waves are generated at an interface between the acoustic matching layer and the acoustic lens, or an interface between the acoustic matching layers, it is possible to prevent the interface reflected waves from being emitted to a measurement target from the acoustic lens later than first waves as described above, and thus to improve a distance resolution.

In other words, if an ultrasonic wave which propagates from a first medium having high acoustic impedance toward a second medium having low acoustic impedance is reflected at an interface between the first medium and the second medium, a phase of the ultrasonic wave is inverted. Therefore, a phase of the ultrasonic wave is inverted when the ultrasonic wave from the acoustic matching layer (first layer) is reflected at an interface with the ultrasonic transducer (vibration film), and when the ultrasonic wave from the first layer is reflected at an interface with the second layer. At this time, in the application example, each of the acoustic matching layers has a thickness corresponding to an odd-numbered multiple of $\lambda/4$, and thus the ultrasonic wave whose phase is inverted and an ultrasonic wave whose phase is not inverted cancel out each other. Therefore, it is possible to prevent an interface reflected wave at each interface located between the ultrasonic transducer and the acoustic lens from being emitted from the acoustic lens toward a measurement target, and thus to improve a distance resolution.

In the ultrasonic device according to the application example, it is preferable that the acoustic matching layer is formed of the single first layer and the single second layer.

In the application example with this configuration, the acoustic matching layer is formed of two layers. In this configuration, for example, compared with a case where the acoustic matching layer is formed of four or more layers, a thickness of the entire acoustic matching layer can be reduced, and thus it is possible to suppress a reduction in an ultrasonic wave emitted from the acoustic lens.

An ultrasonic device according to an application example includes an ultrasonic transducer that has a vibration film and transmits an ultrasonic wave from a first surface side of the vibration film; an acoustic matching layer that is provided on the first surface side of the vibration film; and an acoustic lens that is provided on the acoustic matching layer on an opposite side to the vibration film, in which the acoustic matching layer has acoustic impedance lower than acoustic impedance of the acoustic lens, and has a thickness corresponding to an integer multiple of $\lambda/2$ with a wavelength of the ultrasonic wave as $\lambda$.

In this application example, the acoustic matching layer has a thickness corresponding to an integer multiple of $\lambda/2$ with a wavelength of the ultrasonic wave transmitted from the ultrasonic transducer as $\lambda$. The acoustic matching layer has acoustic impedance lower than that of the acoustic lens.

In this configuration, even if interface reflected waves are generated at an interface between the acoustic matching layer and the acoustic lens, it is possible to prevent the interface reflected waves from being emitted to a measurement target from the acoustic lens later than first waves, and thus to improve a distance resolution. In other words, in the same manner as in the above-described application example, a phase of the interface reflected waves can be made reverse to a phase of the first waves, and thus the interface reflected waves can be canceled out by the first waves.

It is preferable that the ultrasonic device according to the application example further includes an intermediate layer that is disposed between the acoustic matching layer and the acoustic lens, the intermediate layer is formed of even-numbered layers including a first intermediate layer having acoustic impedance higher than acoustic impedance of the acoustic matching layer and a second intermediate layer having acoustic impedance lower than acoustic impedance of each of the first intermediate layer and the acoustic lens, and the first intermediate layer and the second intermediate layer are disposed in this order toward the acoustic lens from the vibration film, and each of the first intermediate layer and the second intermediate layer has a thickness corresponding to an odd-numbered multiple of $\lambda/4$.

In the application example with this configuration, the intermediate layer is disposed between the acoustic matching layer and the acoustic lens. The intermediate layer is formed of even-numbered layers such as the first intermediate layer and the second intermediate layer which are disposed in this order from the acoustic matching layer side. The first intermediate layer has acoustic impedance higher than that of the acoustic matching layer, and the second intermediate layer has acoustic impedance lower than that of each of the first intermediate layer and the acoustic lens. Each of the first intermediate layer and the second intermediate layer has a thickness corresponding to an odd-numbered multiple of $\lambda/4$ with a wave length of the ultrasonic wave transmitted from the ultrasonic transducer as $\lambda$.

In this configuration, in the same manner as in the above-described application example, even if interface reflected waves are generated at an interface between the acoustic matching layer and the intermediate layer, an interface between the first intermediate layer and the second intermediate layer, and an interface between the intermediate layer and the acoustic lens, it is possible to prevent the interface reflected waves from being emitted to a measurement target from the acoustic lens later than first waves, and thus to improve a distance resolution.

In the ultrasonic device according to the application example, it is preferable that the intermediate layer is formed of the single first intermediate layer and the single second intermediate layer.

In the application example with this configuration, the intermediate layer is formed of two layers. In this configuration, for example, compared with a case where the intermediate layer is formed of four or more layers, a thickness of the entire intermediate layer can be reduced, and thus it is possible to suppress attenuation of the first waves.

In the ultrasonic device according to the application example, it is preferable that the vibration film has the first surface which is planar, and a surface of the acoustic matching layer on the vibration film side, a surface of the acoustic matching layer on the acoustic lens side, and a surface of the acoustic lens on the acoustic matching layer side are parallel to the first surface.

In the application example with this configuration, the vibration film has the planar first surface, and each interface is planar and is parallel to the first surface. Consequently, for example, compared with a case where an interface is not planar, it is possible to more reliably cancel out interface reflected waves regardless of a reflection position of the interface reflected waves at each interface in a surface direction, and thus to improve a distance resolution. In other words, in a case where the interface is not planar and is not parallel, interface reflected waves are reflected in a direction corresponding to a reflect ion position, and thus a propagation distance changes according to the reflection position. Consequently, there is concern that a phase of the interface reflected wave when being incident to an interface again may not be reverse to a phase of the first waves, and thus the interface reflected waves may not be canceled out. In the application example, interface reflected waves are reflected in a normal direction to the interface regardless of a reflection position, and thus it is possible to prevent the occurrence of the problem, and to more reliably cancel out the interface reflected waves with the first waves.

In the ultrasonic device according to the application example, it is preferable that the ultrasonic transducer includes a piezoelectric element provided on a second surface side of the vibration film opposite to the first surface.

In the application example with this configuration, the ultrasonic transducer includes the piezoelectric element provided on the second surface of the vibration film opposite to the first surface on which the acoustic matching layer is provided. The vibration film is driven by driving the piezoelectric element, and thus an ultrasonic wave can be transmitted from the first surface side.

In this configuration, an interface between the acoustic matching layer and the ultrasonic transducer is formed of the planar first surface, and thus it is possible to improve the flatness of the interface between the acoustic matching layer and the ultrasonic transducer. Therefore, it is possible to make a distance between interfaces more uniform and thus to more reliably cancel out interface reflected waves.

In the ultrasonic device according to the application example, it is preferable that the ultrasonic transducer includes a substrate supporting the vibration film, the substrate includes an opening which is closed by the vibration film and is open on an opposite side to the vibration film, and at least a part of the acoustic matching layer is disposed inside the opening.

In the application example with this configuration, the ultrasonic transducer includes the opening closed by the vibration film, and includes the substrate closing the vibration film. At least apart of the acoustic matching layer adjacent to the vibration film is disposed inside the opening. In this configuration, for example, in a case where the acoustic matching layer is formed of a single layer, the entire acoustic matching layer is disposed in the opening, and, in a case where the acoustic matching layer is formed of a plurality of layers, a single layer on the vibration film side is disposed in the opening. Therefore, it is possible to adjust a thickness of the acoustic matching layer according to a thickness of the opening, and also the adjustment is easy.

It is preferable that the ultrasonic device according to the application example further includes an adjustment member that is disposed on the substrate on the acoustic lens side, and adjusts a thickness of the acoustic matching layer.

In the application example with this configuration, the ultrasonic device includes the adjustment member adjusting a thickness of the acoustic matching layer. In this configuration, for example, it is possible to easily adjust a thickness of the acoustic matching layer by adjusting a thickness of the adjustment member. It is possible to easily set a thickness of the acoustic matching layer to an appropriate value.

An ultrasonic module according to this application example includes an ultrasonic device including an ultrasonic transducer that has a vibration film and transmits an ultrasonic wave from a first surface side of the vibration film, an acoustic matching layer that is provided on the first surface side of the vibration film, and an acoustic lens that is provided on the acoustic matching layer on an opposite side to the vibration film; and a circuit board on which the ultrasonic device is provided, in which the acoustic matching layer is formed of even-numbered layers including a first layer and a second layer having acoustic impedance lower than acoustic impedance of each of the first layer and the acoustic lens, and the first layer and the second layer are disposed in this order toward the acoustic lens from the vibration film, and in which each of the first layer and the second layer has a thickness corresponding to an odd-numbered multiple of $\lambda/4$ with a wavelength of the ultrasonic wave as $\lambda$.

In this application example, the acoustic matching layer is formed of even-numbered layers such as the first layer and the second layer which are disposed in this order from the vibration film side. Each of the first layer and the second layer has a thickness corresponding to an odd-numbered multiple of $\lambda/4$ with a wavelength of the ultrasonic wave transmitted from the ultrasonic transducer as $\lambda$. The second layer has acoustic impedance lower than that of each of the first layer and the acoustic lens.

In this configuration, in the same manner as in the application example related to the ultrasonic device, even if interface reflected waves are generated at an interface between the acoustic matching layer and the acoustic lens, or an interface between the acoustic matching layers, it is possible to prevent the interface reflected waves from being emitted to a measurement target from the acoustic lens later than first waves as described above, and thus to improve a distance resolution.

An ultrasonic module according to this application example includes an ultrasonic device including an ultrasonic transducer that has a vibration film and transmits an ultrasonic wave from a first surface side of the vibration film, an acoustic matching layer that is provided on the first surface side of the vibration film, and an acoustic lens that is provided on the acoustic matching layer on an opposite side to the vibration film; and a circuit board on which the ultrasonic device is provided, in which the acoustic matching layer has acoustic impedance lower than acoustic impedance of the acoustic lens, and has a thickness corresponding to an integer multiple of $\lambda/2$ with a wavelength of the ultrasonic wave as $\lambda$.

In this application example, the acoustic matching layer has a thickness corresponding to an integer multiple of $\lambda/2$ with a wavelength of the ultrasonic wave transmitted from the ultrasonic transducer as $\lambda$. The acoustic matching layer has acoustic impedance lower than that of the acoustic lens.

In this configuration, in the same manner as in the ultrasonic device related to the application example, even if interface reflected waves are generated at an interface between the acoustic matching layer and the acoustic lens, it is possible to prevent the interface reflected waves from being emitted to a measurement target from the acoustic lens later than first waves, and thus to improve a distance resolution.

An ultrasonic measurement apparatus according to this application example includes an ultrasonic device including an ultrasonic transducer that has a vibration film and transmits an ultrasonic wave from a first surface side of the vibration film, an acoustic matching layer that is provided on the first surface side of the vibration film, and an acoustic lens that is provided on the acoustic matching layer on an opposite side to the vibration film; and a control unit that controls the ultrasonic device, in which the acoustic matching layer is formed of even-numbered layers including a first layer and a second layer having acoustic impedance lower than acoustic impedance of each of the first layer and the acoustic lens, and the first layer and the second layer are disposed in this order toward the acoustic lens from the vibration film, and in which each of the first layer and the second layer has a thickness corresponding to an odd-numbered multiple of $\lambda/4$ with a wavelength of the ultrasonic wave as $\lambda$.

In this application example, the acoustic matching layer is formed of even-numbered layers such as the first layer and the second layer which are disposed in this order from the vibration film side. Each of the first layer and the second layer has a thickness corresponding to an odd-numbered multiple of $\lambda/4$ with a wavelength of the ultrasonic wave transmitted from the ultrasonic transducer as $\lambda$. The second layer has acoustic impedance lower than that of each of the first layer and the acoustic lens.

In this configuration, in the same manner as in the application example related to the ultrasonic device, even if interface reflected waves are generated at an interface between the acoustic matching layer and the acoustic lens, or an interface between the acoustic matching layers, it is possible to prevent the interface reflected waves from being emitted to a measurement target from the acoustic lens later than first waves as described above, and thus to improve a distance resolution.

An ultrasonic measurement apparatus according to this application example includes an ultrasonic device including an ultrasonic transducer that has a vibration film and transmits an ultrasonic wave from a first surface side of the vibration film, an acoustic matching layer that is provided on the first surface side of the vibration film; and an acoustic lens that is provided on the acoustic matching layer on an opposite side to the vibration film, and a control unit that controls the ultrasonic device, in which the acoustic matching layer has acoustic impedance lower than acoustic impedance of the acoustic lens, and has a thickness corresponding to an integer multiple of $\lambda/2$ with a wavelength of the ultrasonic wave as $\lambda$.

In this application example, the acoustic matching layer has a thickness corresponding to an integer multiple of $\lambda/2$ with a wavelength of the ultrasonic wave transmitted from the ultrasonic transducer as $\lambda$. The acoustic matching layer has acoustic impedance lower than that of the acoustic lens.

In this configuration, in the same manner as in the ultrasonic device related to the application example, even if interface reflected waves are generated at an interface between the acoustic matching layer and the acoustic lens, it is possible to prevent the interface reflected waves from being emitted to a measurement target from the acoustic lens later than first waves, and thus to improve a distance resolution.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, an ultrasonic apparatus according to a first embodiment will be described with reference to the drawings.

Configuration of Ultrasonic Measurement Apparatus

Figure 1:
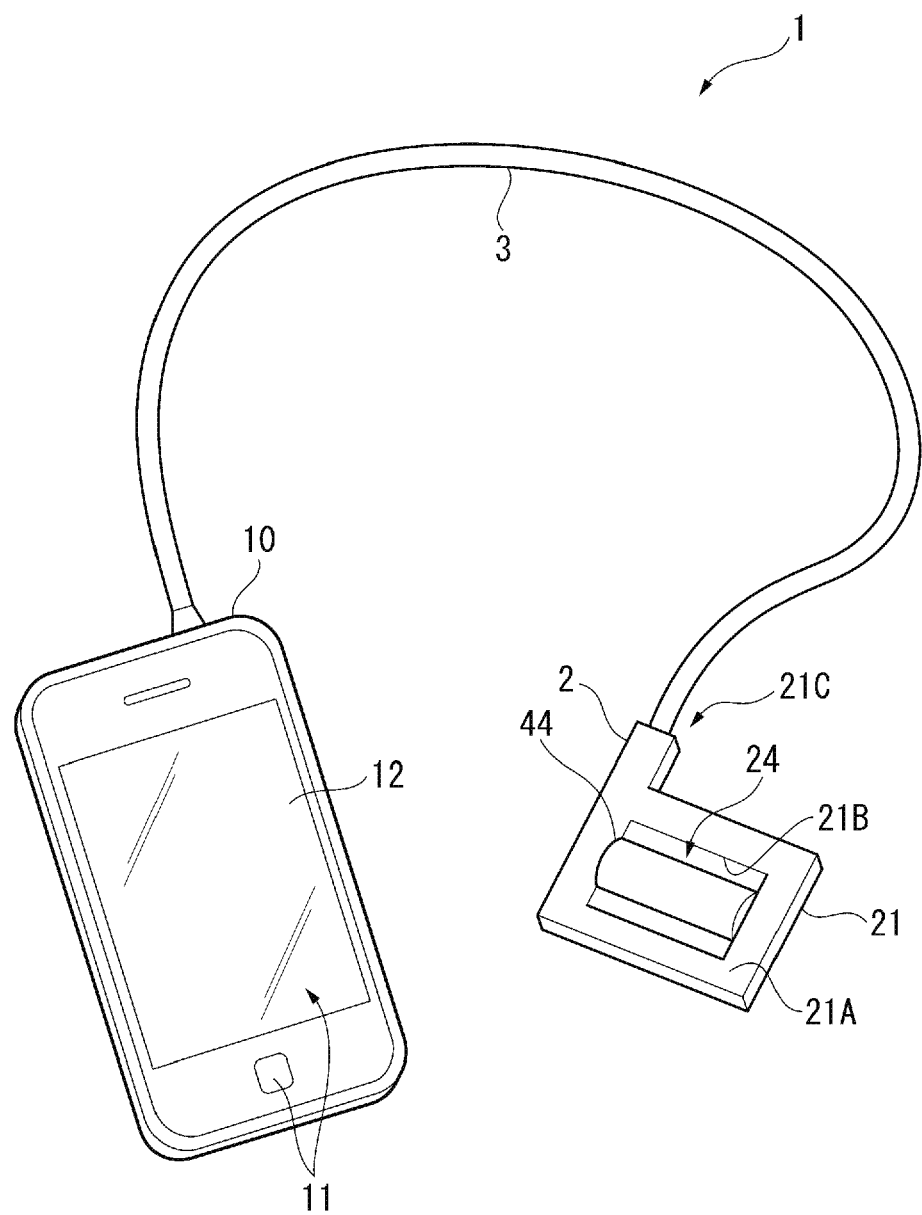
FIG. 1 is a diagram illustrating a schematic configuration of an ultrasonic apparatus according to a first embodiment.

FIG. 1 is a perspective view illustrating a schematic configuration of an ultrasonic measurement apparatus 1 according to the present embodiment.

The ultrasonic measurement apparatus 1 of the present embodiment corresponds to an electronic apparatus, and includes, as illustrated in FIG. 1, an ultrasonic probe 2 and a control device 10 which is electrically connected to the ultrasonic probe 2 via a cable 3.

The ultrasonic measurement apparatus 1 sends ultrasonic waves into a living body from the ultrasonic probe 2 in a state in which the ultrasonic probe 2 is brought into contact with a surface of the living body (human body). Ultrasonic waves reflected from an organ in the living body are received by the ultrasonic probe 2, and, for example, an internal tomographic image of the living body is obtained or a state (for example, a blood flow) of an organ in the living body is measured, on the basis of a received signal.

Configuration of Control Device

As illustrated in FIG. 1, the control device 10 includes, for example, an operation unit 11 and a display unit 12. Although not illustrated, the control device 10 includes a storage unit formed of a memory or the like, and a calculation unit formed of a central processing unit (CPU) or the like. The calculation unit reads various programs stored in the storage unit and executes the programs, and, thus, for example, the control device 10 outputs a command for controlling driving of the ultrasonic probe 2, forms an image of an internal structure of a living body and displays the image on the display unit 12 on the basis of a received signal which is input from the ultrasonic probe 2, or measures biological information such as a blood flow and displays the biological information on the display unit 12. In other words, the control device 10 corresponds to a control unit. As the control device 10, for example, a terminal device such as a tablet terminal, a smart phone, or a personal computer may be used, and a dedicated terminal device for operating the ultrasonic probe 2 may be used.

Configuration of Ultrasonic Probe

Figure 2:
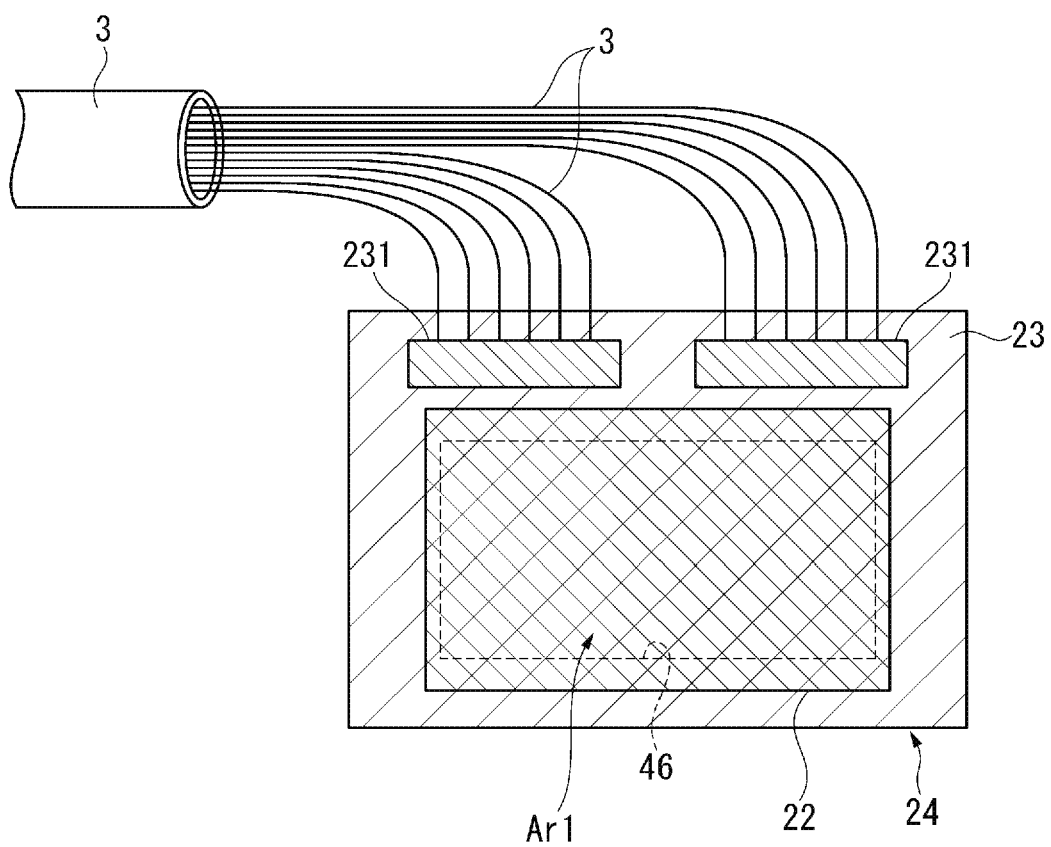
FIG. 2 is a plan view illustrating a schematic configuration of an ultrasonic sensor in the first embodiment.

FIG. 2 is a plan view illustrating a schematic configuration of an ultrasonic sensor 24 of the ultrasonic probe 2.

The ultrasonic probe 2 includes a casing 21 (refer to FIG. 1), an ultrasonic device 22 provided in the casing 21, and a wiring board 23 on which a driver circuit and the like for controlling the ultrasonic device 22 are provided. The ultrasonic sensor 24 (corresponding to an ultrasonic module) is formed of the ultrasonic device 22 and the wiring board 23.

Configuration of Casing

As illustrated in FIG. 1, the casing 21 is formed in a rectangular box shape in a plan view, and is provided with a sensor window 21B on one surface (sensor surface 21A) which is orthogonal to a thickness direction, and a part of the ultrasonic device 22 is exposed to one surface. A passing hole 21C of the cable 3 is provided at a part (a side surface in the example illustrated in FIG. 1) of the casing 21. The cable 3 is inserted into the casing 21 through the passing hole 21C so as to be connected to a connector 231 (refer to FIG. 2) of the wiring board 23. A gap between the cable 3 and the passing hole 21C is filled with, for example, a resin material, and thus water resistance is ensured.

In the present embodiment, a configuration example in which the ultrasonic probe 2 is connected to the control device 10 via the cable 3 is described, but this is only an example, and, for example, the ultrasonic probe 2 and the control device 10 may be connected to each other via wireless communication, and various constituent elements of the control device 10 may be provided in the ultrasonic probe 2.

Configuration of Wiring Board

The wiring board 23 corresponds to a circuit board, and includes terminal portions which are electrically connected to electrode pads 414P and 416P (refer to FIG. 3) provided in the ultrasonic device 22.

The wiring board 23 is provided with a driver circuit and the like for driving the ultrasonic device 22. Specifically, the wiring board is provided with a transmission circuit for transmitting an ultrasonic wave from the ultrasonic device 22, and a reception circuit for processing a received signal when the ultrasonic device 22 receives an ultrasonic wave. The wiring board is connected to the control device 10 via the cable 3 or the like, and thus drives the ultrasonic device 22 on the basis of a command from the control device 10.

Configuration of Ultrasonic Device

Figure 3:
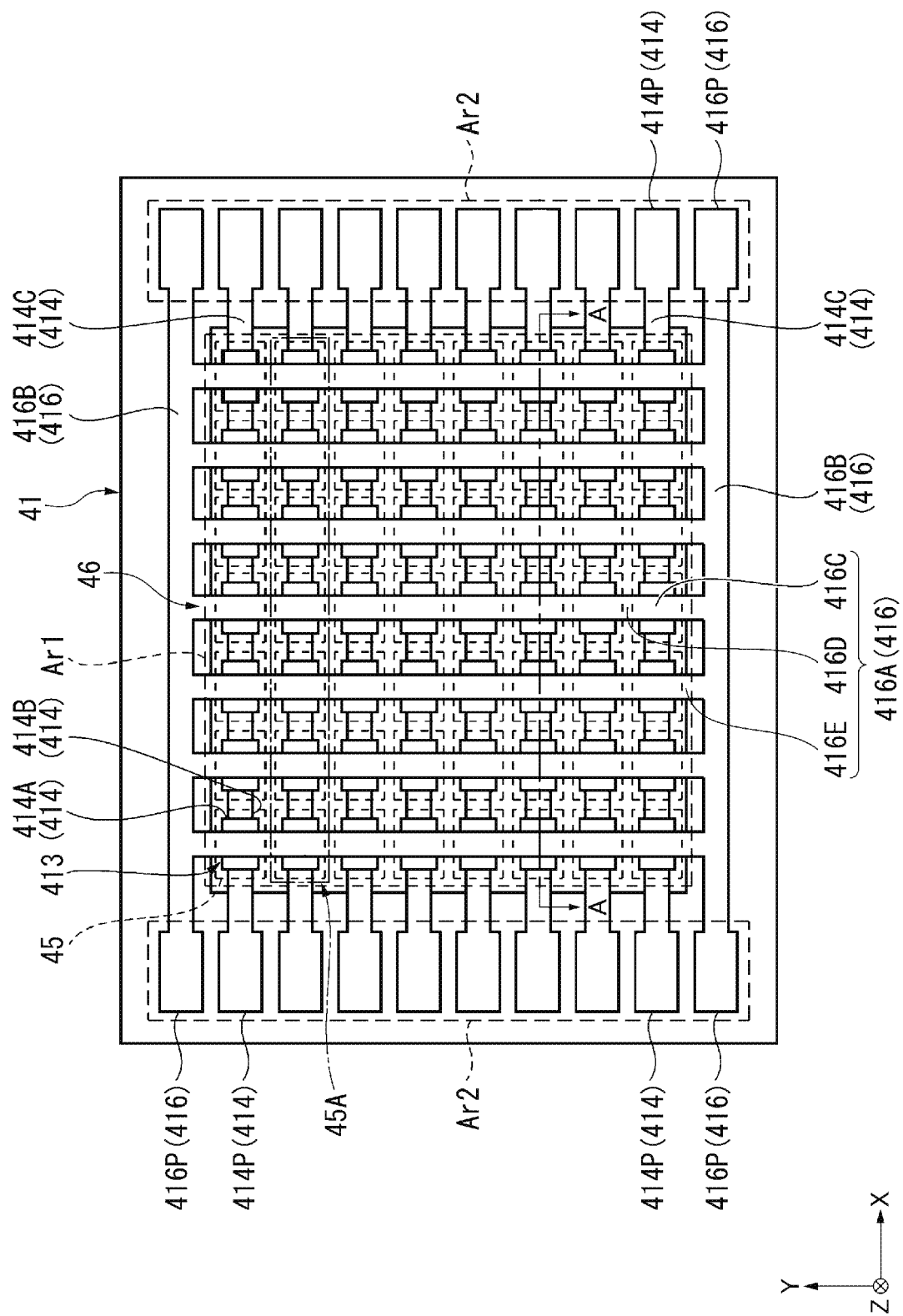
FIG. 3 is a plan view in which an element substrate of an ultrasonic device in the first embodiment is viewed from a sealing plate side.
Figure 4:
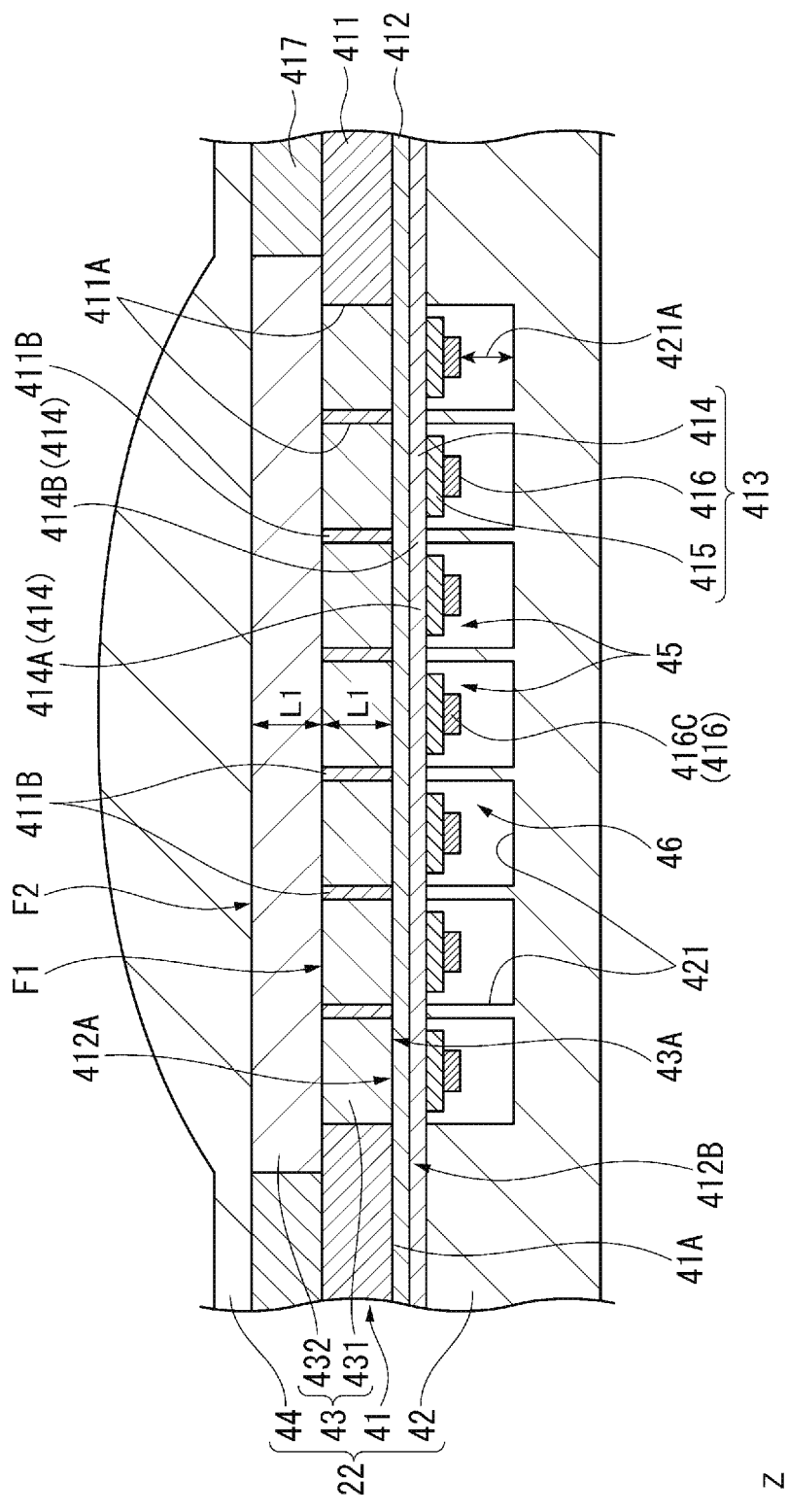
FIG. 4 is a sectional view of the ultrasonic device taken along the line A-A in FIG. 3.

FIG. 3 is a plan view in which an element board 41 of the ultrasonic device 22 is viewed from a sealing plate 42 side. FIG. 4 is a sectional view of the ultrasonic device 22 taken along the line A-A in FIG. 3.

As illustrated in FIG. 4, the ultrasonic device 22 is formed of the element board 41, the sealing plate 42, an acoustic matching layer 43, and an acoustic lens 44.

Configuration of Element Board

As illustrated in FIG. 4, the element board 41 includes a board main body portion 411, a vibration film 412 provided on the sealing plate 42 side of the board main body portion 411, a piezoelectric element 413 provided at the vibration film 412, and an adjustment member 417 adjusting a thickness of a second layer 432 of the acoustic matching layer 43 which will be described later. Here, in the following description, a surface opposing the sealing plate 42 of the element board 41 will be referred to as a rear surface 41A. A surface (first surface) of the vibration film 412 opposite to the sealing plate 42 will be referred to as an ultrasonic wave transmission/reception surface 412A, and a surface (second surface) thereof on the sealing plate 42 side will be referred to as an operation surface 412B. In a plan view in which the element board 41 is viewed from a board thickness direction, a central region of the element board 41 is an array region Ar1, and a plurality of ultrasonic transducers 45 are disposed in a matrix form in the array region Ar1.

The board main body portion 411 is a board supporting the vibration film 412, and is formed of, for example, a semiconductor substrate such as Si. An opening 411A corresponding to each of the ultrasonic transducers 45 is provided in the array region Ar1 of the board main body portion 411. Each opening 411A is closed by the vibration film 412 provided on the rear surface 41A side of the board main body portion 411. As will be described later, the opening 411A is filled with a first layer 431 of the acoustic matching layer 43, and thus a depth dimension of the opening 411A matches a thickness dimension of the first layer 431. Therefore, the thickness dimension of the first layer 431 can be adjusted according to the depth dimension of the opening 411A.

The vibration film 412 is made of, for example, $SiO_2$ or a laminate of $SiO_2$ and $ZrO_2$, and is provided to entirely cover the board main body portion 411 on the rear surface 41A side. A thickness dimension of the vibration film 412 is sufficiently smaller than that of the board main body portion 411. In a case where the board main body portion 411 is made of Si, and the vibration film 412 is made of $SiO_2$, for example, the board main body portion 411 on the rear surface 41A side is subjected to an oxidation process, and thus the vibration film 412 with a desired thickness dimension can be easily formed. In this case, the board main body portion 411 is subjected to an etching process by using the vibration film 412 of $SiO_2$ as an etching stopper, and thus it is possible to easily form the opening 411A.

As illustrated in FIG. 4, the piezoelectric element 413 which is a laminate of a lower electrode 414, a piezoelectric film 415, and an upper electrode 416 is provided on the vibration film 412 (rear surface 41A side) closing each opening 411A. Here, a single ultrasonic transducer 45 is formed of the vibration film 412 closing the opening 411A and the piezoelectric element 413.

In the ultrasonic transducer 45, a rectangular wave voltage with a predetermined frequency is applied between the lower electrode 414 and the upper electrode 416 so that the vibration film 412 in an opening region of the opening 411A vibrates, and thus an ultrasonic wave can be sent from the ultrasonic wave transmission/reception surface 412A side. If the vibration film 412 vibrates due to an ultrasonic wave which is reflected from a target object and is incident from the ultrasonic wave transmission/reception surface 412A side, a potential difference occurs between an upper part and a lower part of the piezoelectric film 415. Therefore, the received ultrasonic wave can be detected by detecting the potential difference occurring between the lower electrode 414 and the upper electrode 416.

In the present embodiment, as illustrated in FIG. 3, a plurality of ultrasonic transducers 45 are disposed along an X direction (slice direction) and a Y direction (scan direction) intersecting (in the present embodiment, orthogonal to) the X direction in the predetermined array region Ar1 of the element board 41, so as to form an ultrasonic transducer array 46. The ultrasonic transducer array 46 corresponds to an ultrasonic wave transmission/reception unit.

Here, the lower electrode 414 is formed in a linear shape along the X direction. In other words, the lower electrode 414 is provided to cross the plurality of ultrasonic transducers 45 arranged along the X direction, and is formed of a lower electrode main body 414A located between the piezoelectric film 415 and the vibration film 412, a lower electrode line 414B connecting adjacent lower electrode main bodies 414A to each other, and a lower terminal electrode line 414C extracted to each of terminal regions Ar2 other than the array region Ar1. Therefore, in the ultrasonic transducers 45 arranged in the X direction, the lower electrodes 414 have the same potential.

The lower terminal electrode line 414C extends to the terminal region Ar2 other than the array region Ar1 so as to form the first electrode pad 414P in the terminal region Ar2. The first electrode pad 414P is connected to a terminal portion provided on the wiring board.

On the other hand, as illustrated in FIG. 3, the upper electrode 416 includes element electrode portions 416A provided to cross the plurality of ultrasonic transducers 45 along the Y direction, and a common electrode portion 416B connecting ends of the plurality of element electrode portions 416A to each other. Each of the element electrode portions 416A includes an upper electrode main body 416C laminated on the piezoelectric film 415, an upper electrode line 416D connecting adjacent upper electrode main bodies 416C to each other, and an upper terminal electrode 416E extending outward along the Y direction from the ultrasonic transducers 45 which are disposed at both ends in the Y direction.

The common electrode portion 416B is provided at each of a +Y side end and a −Y side end of the array region Ar1. The common electrode portion 416B on the +Y side connects the upper terminal electrodes 416E to each other which extend toward the +Y side from the ultrasonic transducers 45 provided at the +Y side end among the plurality of ultrasonic transducers 45 provided along the Y direction. The common electrode portion 416B at the −Y side end connects the upper terminal electrodes 416E extending toward the −Y side to each other. Therefore, in the respective ultrasonic transducers 45 in the array region Ar1, the upper electrodes 416 have the same potential. The pair of common electrode portions 416B is provided along the X direction, and ends thereof are extracted to the terminal regions Ar2 from the array region Ar1. The common electrode portions 416B form second electrode pads 416P connected to the terminal portions of the wiring board in the terminal regions Ar2.

In the ultrasonic transducer array 46, a single ultrasonic transducer group 45A is formed of ultrasonic transducers 45 which are connected to each other via the lower electrode 414 and are arranged in the X direction, and a plurality of ultrasonic transducer groups 45A are arranged along the Y direction so as to form a one-dimensional array structure.

The adjustment member 417 adjusts a thickness of the second layer 432 of the acoustic matching layer 43 which will be described later, and is disposed to surround the array region Ar1 in which the openings 411A are formed, on a +Z side of the board main body portion 411. The region surrounded by the adjustment member 417 is filled with the second layer 432, and a thickness dimension of the adjustment member 417 matches a thickness dimension of the second layer 432. Therefore, a thickness of the second layer 432 can be adjusted by using a thickness of the adjustment member 417.

Configuration of Sealing Plate

A planar shape of the sealing plate 42 viewed from the thickness direction is formed to be the same as, for example, that of the element board 41, and is formed of a semiconductor substrate such as Si or an insulator substrate. A material or a thickness of the sealing plate 42 influences frequency characteristics of the ultrasonic transducer 45, and is thus preferably set on the basis of a center frequency of an ultrasonic wave which is transmitted and received in the ultrasonic transducer 45.

The sealing plate 42 is provided with a plurality of grooves 421 corresponding to the openings 411A of the element board 41 in an array opposing region which opposes the array region Ar1 of the element board 41. Consequently, a gap 421A having a predetermined dimension is provided between the vibration film 412 and the element board 41 in a region (inside the opening 411A) which is subjected to vibration due to the ultrasonic transducer 45, and thus vibration of the vibration film 412 is not hindered. It is possible to prevent a problem (crosstalk) that a back wave from a single ultrasonic transducer 45 is incident to another ultrasonic transducer 45 adjacent thereto.

If the vibration film 412 vibrates, an ultrasonic wave as a back wave is emitted not only to the opening 411A side (ultrasonic wave transmission/reception surface 412A side) but also to the sealing plate 42 side (rear surface 41A side). The back wave is reflected by the sealing plate 42, and is emitted to the vibration film 412 side again via the gap 421A. In this case, if phases of the reflected back wave and the ultrasonic wave emitted to the ultrasonic wave transmission/reception surface 412A from the vibration film 412 are deviated relative to each other, the ultrasonic wave attenuates. Therefore, in the present embodiment, a depth of each of the grooves 421 is set so that an acoustic distance in the gap 421A is an odd-numbered multiple of $\lambda/4$ when a wavelength of the ultrasonic wave is indicated by $\lambda$. In other words, a thickness dimension of each portion of the element board 41 or the sealing plate 42 is set by taking into consideration the wavelength $\lambda$ of an ultrasonic wave emitted from the ultrasonic transducer 45.

The sealing plate 42 may have a configuration in which openings (not illustrated) are provided to correspond to the electrode pads 414P and 416P provided in the terminal regions Ar2 at positions of the element board 41 opposing the terminal regions Ar2. In this case, through electrodes (through-silicon via (TSV)) which penetrate through the sealing plate 42 in the thickness direction are provided in the opening, and thus the electrode pads 414P and 416P are connected to the terminal portions of the wiring board via the through electrodes. There may be a configuration in which flexible printed circuits (FPC), cables, or wires are inserted into the openings so that the electrode pads 414P and 416P are connected to the wiring board.

Configuration of Acoustic Lens

The acoustic lens 44 is provided on the acoustic matching layer 43 (+Z side) which will be described later in detail. The acoustic lens 44 is exposed to the outside from the sensor window 21B of the casing 21 as illustrated in FIG. 1. Acoustic impedance Z3 of the acoustic lens 44 is set to be similar to acoustic impedance of a living body. The acoustic lens 44 comes into close contact with a living body surface so as to cause an ultrasonic wave transmitted from the ultrasonic transducer 45 via the acoustic matching layer 43 to converge in the living body with high efficiency, and to cause an ultrasonic wave reflected inside the living body to propagate toward the ultrasonic transducer 45 with high efficiency. In the present embodiment, the acoustic impedance Z3 is, for example, 1.5 MRayls.

The acoustic lens 44 may be made of, for example, a millable type silicon rubber. The millable type silicon rubber contains, for example, silicon rubber having a dimethyl polysiloxane structure including a vinyl group, silica, and a vulcanizing agent. Specifically, silica is mixed in the silicone rubber as silica particles having a weight average particle size of 15 μm to 30 μm with a mass ratio of 40 mass % to 50 mass % with respect to the silicone rubber. As the vulcanizing agent, for example, 2,5-dimethyl-2,5-ditertiary butyl peroxycyclohexane may be used.

Configuration of Acoustic Matching Layer

As illustrated in FIG. 4, the acoustic matching layer 43 is provided on the ultrasonic wave transmission/reception surface 412A side of the vibration film 412, and includes the first layer 431 on the vibration film 412 and the second layer 432 provided on the first layer 431. The acoustic matching layer 43 causes an ultrasonic wave transmitted from the ultrasonic transducer 45 to propagate toward a living body which is a measurement target with high efficiency, and causes an ultrasonic wave reflected inside the living body to propagate toward the ultrasonic transducer 45 with high efficiency, along with the acoustic lens 44. Thus, the acoustic matching layer 43 is set to acoustic impedance similar to acoustic impedance of a living body. As a material having such acoustic impedance, for example, a silicon resin material such as RTV silicon rubber may be used.

The first layer 431 fills the opening 411A of the element board 41 and is provided on the vibration film 412 (+Z side). In other words, the first layer 431 has a thickness dimension L1 corresponding to a depth dimension of the opening 411A. A surface of the first layer 431 on an opposite side to the vibration film 412, that is, an interface (hereinafter, also referred to as a first interface F1) with the second layer 432 is substantially parallel to the ultrasonic wave transmission/reception surface 412A. A surface 43A of the acoustic matching layer 43 on the vibration film 412 side is in contact with the ultrasonic wave transmission/reception surface 412A, and is parallel to the ultrasonic wave transmission/reception surface 412A. Acoustic impedance Z1 of the first layer 431 is higher than acoustic impedance Z2 of the second layer 432. In the present embodiment, the acoustic impedance Z1 is, for example, 1.5 MRayls, and the acoustic impedance Z2 is, for example, 1 MRayls. A difference between the acoustic impedance Z1 and the acoustic impedance Z2 is preferably set to a value which causes appropriate reflection of an ultrasonic wave between the first layer and the second layer, and is preferably 0.1 MRayls to 1 MRayls, and is more preferably 0.3 MRayls to 0.7 MRayls.

The second layer 432 is provided on the first layer 431 (+Z side), and has the same thickness dimension L1 as that of the first layer 431. A thickness of the second layer 432 is adjusted by setting the thickness dimension of the adjustment member 417 to L1. The surface (that is, the first interface F1) of the second layer 432 on the first layer 431 side and an interface (hereinafter, also referred to as a second interface F2) on the acoustic lens 44 side are substantially parallel to the ultrasonic wave transmission/reception surface 412A.

The acoustic impedance Z2 of the second layer 432 is lower than the acoustic impedance Z1 of the first layer 431 and the acoustic impedance Z3 of the acoustic lens 44. A value of the acoustic impedance may be obtained with a product between density of a medium and sonic speed in the medium. For example, the second layer 432 is formed by using a material having density lower than that of the first layer 431, and thus the acoustic impedance Z2 of the second layer 432 is made lower than the acoustic impedance Z1 of the first layer 431. In the present embodiment, the acoustic impedance Z1 is, for example, 1.5 MRayls.

The thickness dimension L1 of each of the first layer 431 and the second layer 432 is a distance between the ultrasonic wave transmission/reception surface 412A and the first interface F1, and a distance between the first interface F1 and the second interface F2 satisfies the following Equation (1) when a wavelength of an ultrasonic wave transmitted from the ultrasonic transducer 45 is indicated by $\lambda$, and n is an integer of 1 or more. In other words, the first layer 431 and the second layer 432 are formed so that the dimension L1 is an odd-numbered multiple of $\lambda/4$. Operations and effects achieved due to the dimension L1 satisfying the following Equation (1) will be described later.

$$L1=(\lambda/4)\times(2n-1) \qquad (1)$$

Prevention of Tailing Using Acoustic Matching Layer

Here, the ultrasonic device 22 performs ultrasonic measurement by receiving a reflected wave of an ultrasonic wave (hereinafter, referred to as a first wave) which is transmitted from the ultrasonic transducer 45, and propagates through the acoustic matching layer 43 and the acoustic lens 44 so as to be emitted into a living body. In a configuration in which the acoustic matching layer 43 and the acoustic lens 44 are laminated on the ultrasonic wave transmission/reception surface 412A, when ultrasonic measurement is performed, there is concern that an ultrasonic wave (hereinafter, also referred to as a second wave) caused by an interface reflected wave occurring at the interface between the acoustic matching layer 43 and the acoustic lens 44 may be emitted into the living body later than the first wave, and tailing may occur in an ultrasonic wave emitted from the ultrasonic device 22. If the tailing occurs, there is concern that a pulse width of the ultrasonic wave may increase, and thus a distance resolution may be reduced.

In contrast, as will be described later in detail, in the ultrasonic device 22 of the present embodiment, the thickness dimensions (the distance between the ultrasonic wave transmission/reception surface 412A and the first interface F1, and the distance between the first interface F1 and the second interface F2) L1 of the first layer 431 and the second layer 432 of the acoustic matching layer 43 satisfy the above Equation (1). The acoustic impedance Z2 of the second layer 432 is lower than the acoustic impedance Z1 of the first layer 431, and is lower than the acoustic impedance Z3 of the acoustic lens 44. With this configuration, the second wave can be prevented from being emitted into the living body, and thus the distance resolution can be improved.

Figure 5:
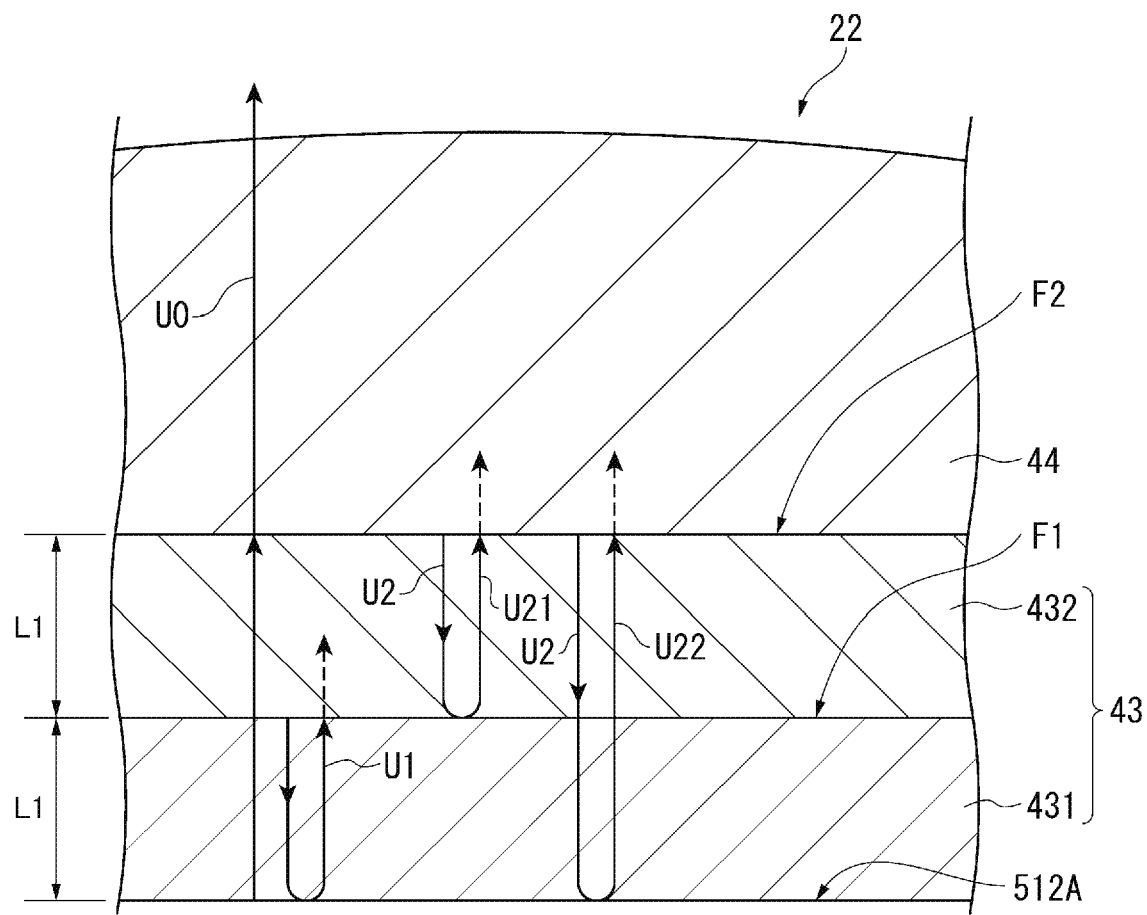
FIG. 5 is a sectional view illustrating a schematic configuration of the ultrasonic device in the first embodiment.

FIG. 5 is a diagram for explaining an operation of preventing tailing caused by an interface reflected wave in the ultrasonic device 22 of the present embodiment, and schematically illustrates sections of the main portions (the acoustic matching layer 43 and the acoustic lens 44) of the ultrasonic device 22. FIG. 5 illustrates a configuration of the ultrasonic device 22 in a simplified manner.

As illustrated in FIG. 5, ultrasonic waves U0 which are transmitted in a normal direction from the ultrasonic transducer 45 and are transmitted through the first interface F1 and the second interface F2 are emitted into a measurement target from the acoustic lens 44. Ultrasonic measurement is performed by detecting reflected waves of the ultrasonic waves U0 with the ultrasonic transducer 45.

Here, as illustrated in FIG. 5, there is a case where some of the ultrasonic waves U0 which are incident to the first interface F1 are reflected at the first interface F1, and thus interface reflected waves U1 are generated. The interface reflected waves U1 are reflected at the ultrasonic wave transmission/reception surface 412A, and reach the first interface F1 again, and, at this time, the interface reflected waves U1 have a reverse phase to a phase of the ultrasonic waves U0. Thus, at least some of the interface reflected waves U1 are canceled out by the ultrasonic waves U0.

Specifically, if ultrasonic waves which are incident to the first interface F1 from the first layer 431 side having acoustic impedance lower than that of the second layer 432 are reflected at the first interface F1, a phase of the ultrasonic waves is inverted. Also when the ultrasonic waves propagate through the first layer 431 and are then reflected at the ultrasonic wave transmission/reception surface 412A, a phase of the ultrasonic waves is inverted. Thus, if a thickness (a distance between the ultrasonic wave transmission/reception surface 412A and the first interface F1) of the first layer 431 is set to an odd-numbered multiple of $\lambda/4$, a phase of the interface reflected waves U1 when being incident to the first interface F1 again can be made reverse to a phase of the ultrasonic waves U0. From the above description, at least some of interface reflected waves U2 which are reflected at the first interface F1 so as to be reflected at the ultrasonic wave transmission/reception surface 412A, and are then incident to the first interface F1 again, are canceled out by the ultrasonic waves U0.

There is a case where some of the ultrasonic waves U0 which are incident to the second interface F2 are reflected at the second interface F2 so that the interface reflected waves U2 are generated, and some of the interface reflected waves U2 are reflected at the first interface F1 so that interface reflected waves U21 are generated. When the interface reflected waves U21 are reflected at the first interface F1 and then reach the second interface F2 again, a phase of the interface reflected waves U21 is reverse to a phase of the ultrasonic waves U0. Thus, at least some of the interface reflected waves U21 are canceled out by the ultrasonic waves U0.

Specifically, if a thickness (a distance between the first interface F1 and the second interface F2) of the second layer 432 is set to an odd-numbered multiple of $\lambda/4$, a phase of the interface reflected waves U21 when being incident to the second interface F2 again can be made reverse to a phase of the ultrasonic waves U0. Therefore, at least some of the interface reflected waves U21 are canceled out by the ultrasonic waves U0 at the second interface F2.

Among the interface reflected waves U2, interface reflected waves U22 which are transmitted through the first interface F1 are transmitted through the first layer 431 so as to be reflected at the ultrasonic wave transmission/reception surface 412A, and then reach the second interface F2 again, and, at this time, a phase thereof is reverse to a phase of the ultrasonic waves U0. Thus, at least some of the interface reflected waves U22 are canceled out by the ultrasonic waves U0. In other words, when the interface reflected waves U22 are reflected at the ultrasonic wave transmission/reception surface 412A, a phase thereof is inverted. Therefore, each of thicknesses of the first layer 431 and the second layer 432 is set to an odd-numbered multiple of $\lambda/4$ (that is, a distance between the second interface F2 and the ultrasonic wave transmission/reception surface 412A is an even-numbered multiple of $\lambda/4$, that is, an integer multiple of $\lambda/2$), and thus a phase of the interface reflected waves U22 when being incident to the second interface F2 again can be made reverse to a phase of the ultrasonic waves U0. Thus, at least some of the interface reflected waves U22 are canceled out by the ultrasonic waves U0 at the second interface F2.

As described above, at least some of the interface reflected waves generated at each of the interfaces F1 and F2 are canceled out, and thus it is possible to prevent the interface reflected waves from being emitted into a living body and thus to improve a distance resolution.

In the present embodiment, the surface 43A of the acoustic matching layer 43 on the vibration film 412 side and the respective interfaces F1 and F2 are substantially parallel to the ultrasonic wave transmission/reception surface 412A, and thus interface reflected waves can be made to propagate in the normal direction (Z direction) to the ultrasonic wave transmission/reception surface 412A and the respective interfaces F1 and F2. Thus, a propagation distance of interface reflected waves can be set to the above-described distance, and thus it is possible to reliably cancel out the interface reflected waves.

Figure 6:
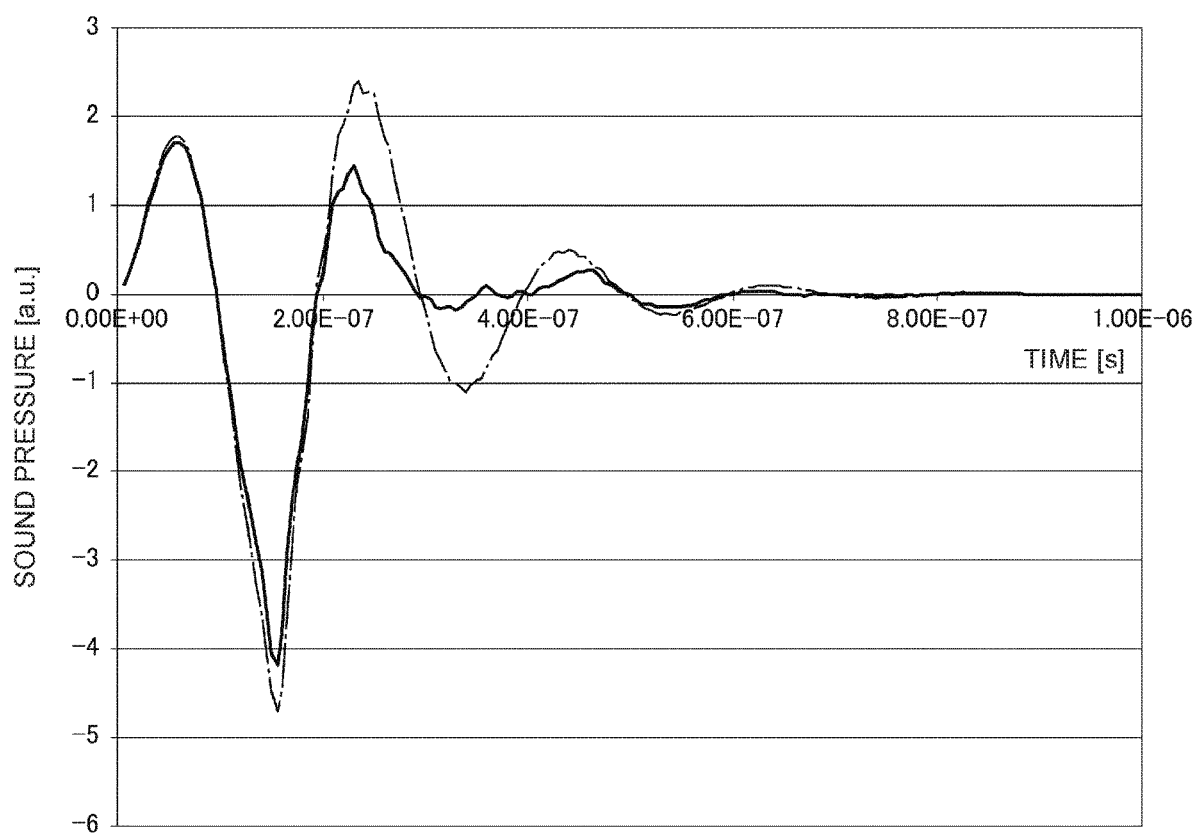
FIG. 6 is a diagram illustrating changes in sound pressure due to ultrasonic waves transmitted from the ultrasonic device according to the first embodiment and an ultrasonic device according to a comparative example.
Figure 7:
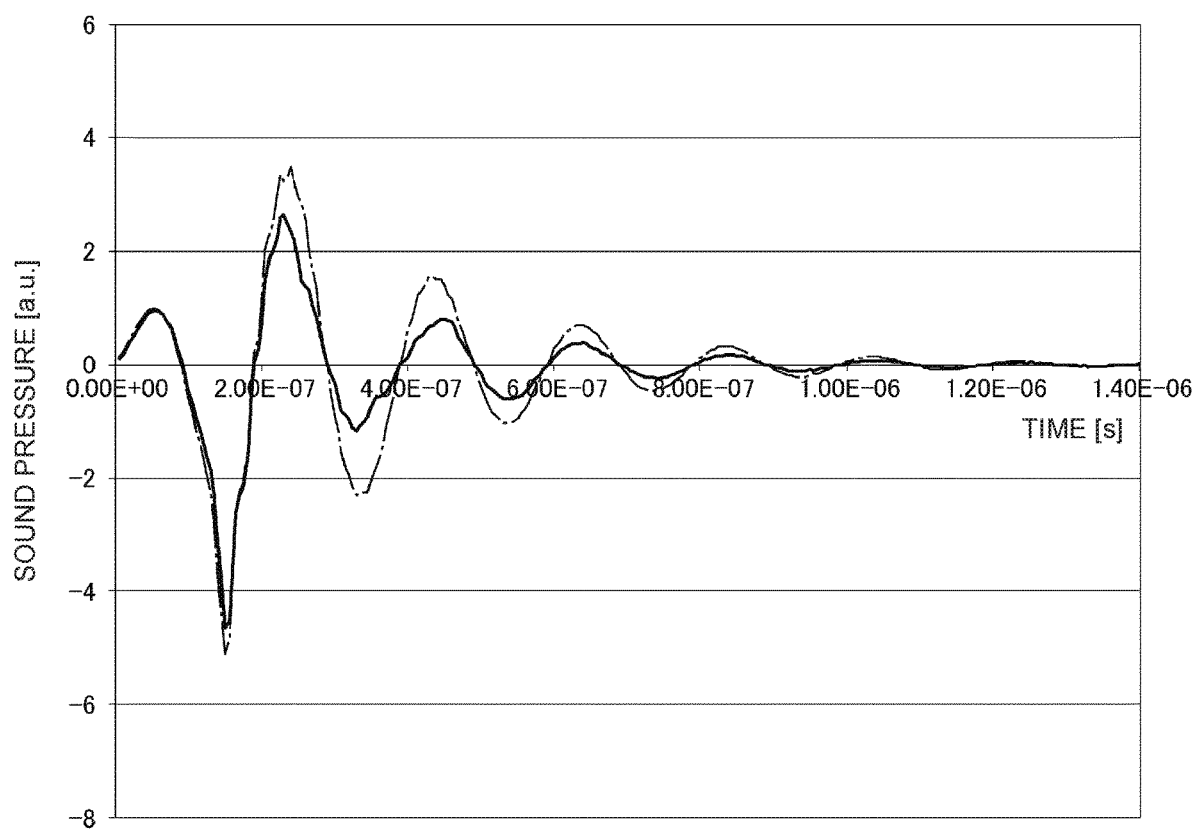
FIG. 7 is a diagram illustrating changes in sound pressure due to ultrasonic waves transmitted from the ultrasonic device according to the first embodiment and an ultrasonic device according to a comparative example.

FIGS. 6 and 7 are diagrams illustrating examples of temporal changes of an ultrasonic wave transmitted from the ultrasonic device. Here, a temporal change of an ultrasonic wave emitted from the ultrasonic device 22 of the present embodiment is indicated by a solid line. On the other hand, a dot chain line illustrates an example of a temporal change of an ultrasonic wave transmitted from an ultrasonic device according to a comparative example, further including an acoustic matching layer whose thickness is not an integer multiple of $\lambda/2$. In FIGS. 6 and 7, values of acoustic impedances of the first layer 431 and the acoustic lens 44 are 1.5 MRayls, and a value of acoustic impedance of the second layer 432 is 1 MRayls.

In the examples illustrated in FIGS. 6 and 7, for example, a drive voltage having a waveform of a burst wave with 5 MHz is applied to the ultrasonic transducer 45, so as to drive the ultrasonic transducer 45. As illustrated in FIG. 6, in a case where a Q value of the ultrasonic device 22 is 2, in the comparative example indicated by the dot chain line, a change in sound pressure is detected after about $3.00 \times 10^{-7}$ sec, and so-called tailing occurs. In contrast, it can be seen from the ultrasonic device 22 of the present embodiment indicated by the solid line that a change in sound pressure is reduced, and thus tailing is prevented.

As illustrated in FIG. 7, also in a case where a Q value of the ultrasonic device 22 is 4, a sound pressure change in a tailing portion is prevented by using the ultrasonic device 22 of the present embodiment compared with the comparative example.

As illustrated in FIG. 5, the ultrasonic waves U0 propagates from the first layer 431 having the high acoustic impedance to the second layer 432 having the low acoustic impedance when passing through the first interface F1, and thus sound pressure is reduced, but, conversely, propagates from the second layer 432 having the low acoustic impedance to the acoustic lens 44 when passing through the second interface F2, and thus sound pressure increases. Therefore, compared with the ultrasonic device of the comparative example including the acoustic matching layer having a single layered configuration, in the ultrasonic device 22 including the acoustic matching layer 43 having a two-layered configuration, it is possible to prevent tailing and also to suppress a reduction in sound pressure.

As illustrated in FIGS. 6 and 7, also in the case of the comparative example, a Q value of the ultrasonic device is reduced, and thus it is possible to reduce a sound pressure change in the tailing portion. However, outputs of the ultrasonic waves U0 are also reduced. In contrast, by using the ultrasonic device 22 of the present embodiment, it is possible to reduce a sound pressure change in the tailing portion even without reducing a Q value. Therefore, according to the ultrasonic device 22, it is possible to suppress a decline in output of the ultrasonic waves U0, to reduce the influence of tailing, and thus to perform ultrasonic measurement with high accuracy.

Manufacturing Method of Ultrasonic Device

Next, a description will be made of a manufacturing method of the ultrasonic device 22 as described above.

Figure 8:
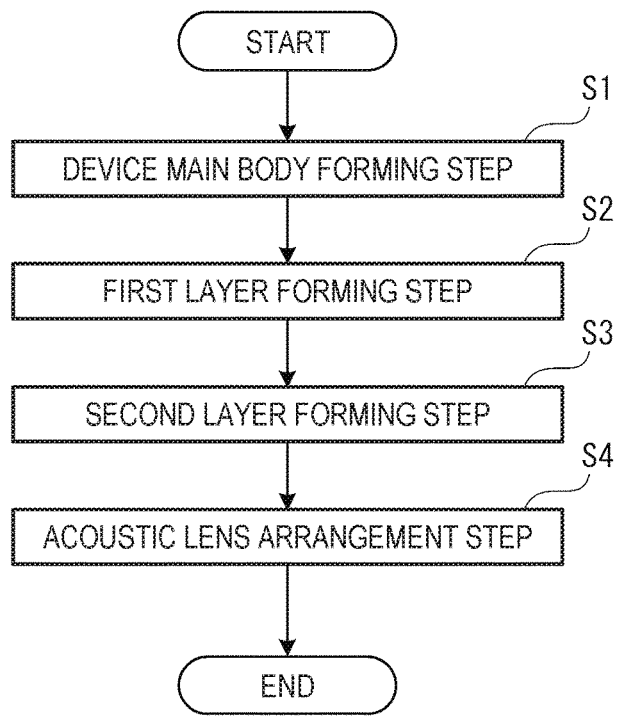
FIG. 8 is a flowchart illustrating an example of a manufacturing method of the ultrasonic device according to the first embodiment.
Figure 9:
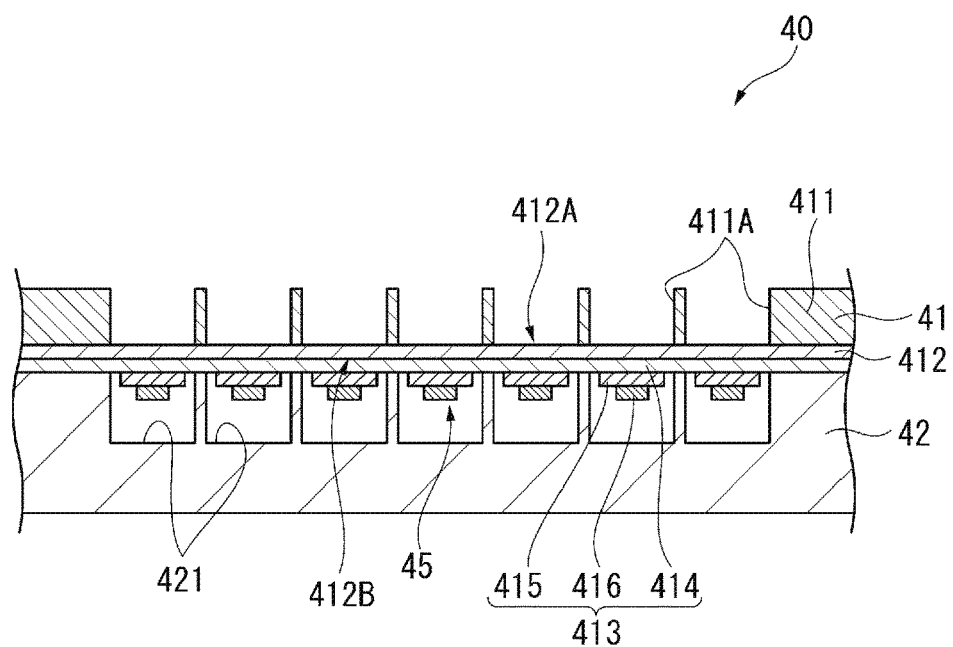
FIG. 9 is a diagram illustrating manufacturing steps of the ultrasonic device according to the first embodiment.
Figure 10:
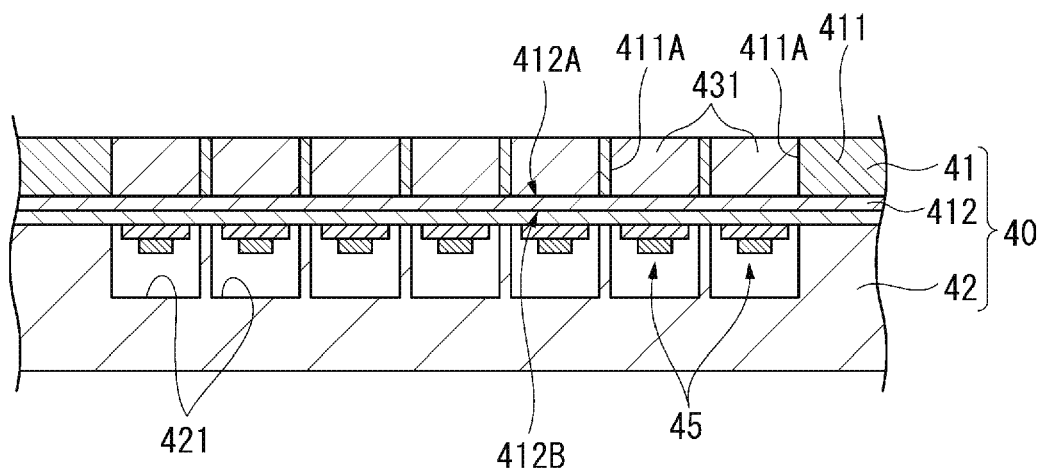
FIG. 10 is a diagram illustrating manufacturing steps of the ultrasonic device according to the first embodiment.
Figure 11:
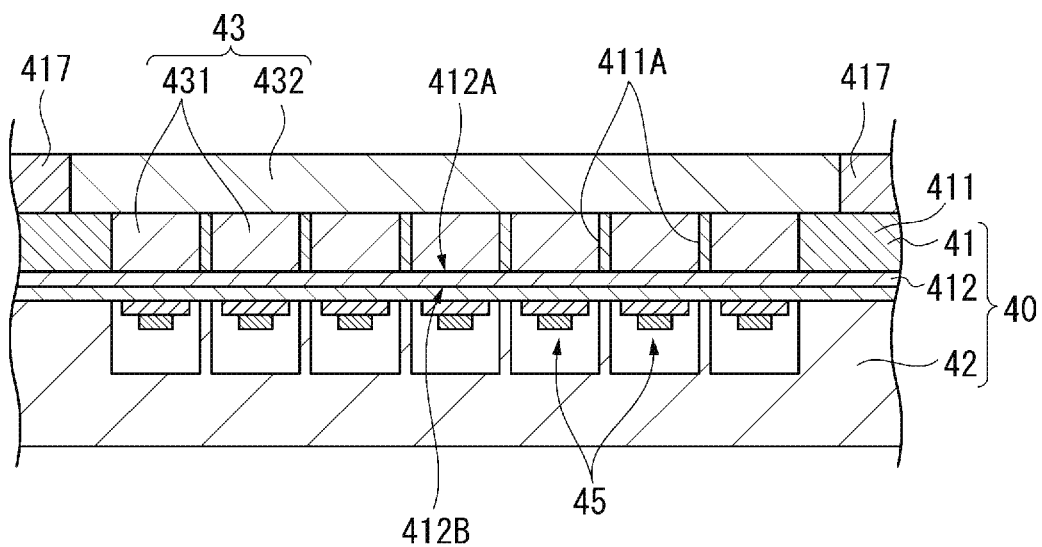
FIG. 11 is a diagram illustrating manufacturing steps of the ultrasonic device according to the first embodiment.

FIG. 8 is a flowchart illustrating respective steps in manufacturing of the ultrasonic sensor 24 of the present embodiment. FIGS. 9 to 11 are diagrams illustrating the schematic ultrasonic sensor 24 in each step.

In order to manufacture the ultrasonic sensor 24, as illustrated in FIG. 8, a device main body forming step S1, a first layer forming step S2, a second layer forming step S3, and an acoustic lens arrangement step S4 are performed.

In the device main body forming step S1, a device main body 40 (refer to FIG. 9) including the element board 41 and the sealing plate 42 is formed.

In step S1, the vibration film 412 is formed on the board main body portion 411, the piezoelectric element 413 is formed on the vibration film 412, and the openings 411A are formed in the board main body portion 411. At this time, the opening 411A is formed so that a depth thereof is the same as a thickness of the first layer 431. Thereafter, the sealing plate 42 is formed, and the sealing plate 42 is bonded to the device main body 40.

Next, the first layer forming step S2 is performed. In step S2, as illustrated in FIG. 10, the first layer 431 of the acoustic matching layer 43 is formed in the opening 411A of the device main body 40. Specifically, a material forming the first layer 431 fills the inside of the opening 411A. A residual forming material protruding out of the opening 411A is removed so that surfaces of the opening 411A and the first layer 431 on the +Z side are coplanar.

Next, the second layer forming step S3 is performed. In step S3, as illustrated in FIG. 11, the adjustment member 417 is disposed on the board main body portion 411. A thickness of the adjustment member 417 is formed to be the same as a thickness of the second layer 432. Thereafter, a material forming the second layer 432 fills a region surrounded by the adjustment member 417. A protruding residual forming material is removed so that surfaces of the adjustment member 417 and the second layer 432 on the +Z side are coplanar.

Next, the acoustic lens arrangement step S4 is performed, and the acoustic lens 44 is disposed on the second layer 432 on the +Z side. In the above-described way, the ultrasonic device 22 is formed.

In the above-described method of forming the ultrasonic device 22, the element board 41 is bonded to the sealing plate 42, then the acoustic matching layer 43 is formed, and the acoustic lens 44 is disposed, but any other method may be used. In other words, the acoustic matching layer 43 may be formed on the element board 41 before being bonded to the sealing plate 42, and the acoustic lens 44 may be disposed.

The adjustment member 417 is disposed on the element board 41, and then the second layer 432 is formed, but this is only an example, and the second layer 432 may be formed without providing the adjustment member 417. The second layer 432 may be formed on the acoustic lens 44 side instead of being formed on the element board 41 side. In this case, for example, there may be a configuration in which a recess is provided in the acoustic lens 44, the second layer 432 is formed in the recess, and the acoustic lens 44 provided with the second layer 432 is bonded to the element board 41 provided with the first layer 431.

Operations and Effects of First Embodiment

The ultrasonic device 22 of the present embodiment includes the acoustic matching layer 43 provided on the ultrasonic wave transmission/reception surface 412A of the vibration film 412, and the acoustic lens 44 provided on the acoustic matching layer 43. The acoustic matching layer 43 includes the first layer 431 on the ultrasonic wave transmission/reception surface 412A side, and the second layer 432 on the acoustic lens 44 side, and each layer has a thickness corresponding to an odd-numbered multiple of $\lambda/4$ when a wavelength of an ultrasonic wave is indicated by $\lambda$. The acoustic impedance of the second layer 432 is lower than the acoustic impedances of the first layer 431 and the acoustic lens 44. In the ultrasonic device 22 configured as mentioned above, even if interface reflected waves are generated at the respective interfaces F1 and F2 of the acoustic matching layer 43 and the acoustic lens 44 (refer to the interface reflected waves U1 and U2 in FIG. 5), a phase of the interface reflected waves can be made reverse to a phase of the ultrasonic waves U0 transmitted from the ultrasonic transducer 45 as described above when the interface reflected waves are incident to the interfaces again. Therefore, at least some of the interface reflected waves are canceled out, and thus it is possible to prevent the interface reflected waves from being emitted to a measurement target from the acoustic lens 44 later than the ultrasonic waves U0, and thus to improve a distance resolution.

In the present embodiment, the acoustic matching layer 43 is formed of two layers. Here, even in a configuration in which the acoustic matching layer 43 has even-numbered layers, and the first layer 431 and the second layer 432 are alternately disposed, it is possible to prevent the occurrence of tailing caused by interface reflected waves in the same manner. On the other hand, if the acoustic matching layer 43 is thick, attenuation of an ultrasonic wave increases, and thus there is concern that a transmission output of the ultrasonic wave, and further reception sensitivity may be reduced. The entire acoustic matching layer 43 may be thin by making each layer thin, but there is the limitation in making each layer thin. In contrast, the acoustic matching layer 43 is formed of two layers, and thus thinning is easy by thinning the acoustic matching layer 43.

The vibration film 412 has the planar ultrasonic wave transmission/reception surface 412A, and the respective interfaces F1 and F2 are parallel to the ultrasonic wave transmission/reception surface 412A. Here, in a case where the interfaces F1 and F2 are not planar, and are not parallel to the ultrasonic wave transmission/reception surface 412A, interface reflected waves are reflected in a direction corresponding to a reflection position. Thus, a propagation distance changes according to a reflection position of the interface reflected wave, and thus there is concern that a phase of the interface reflected wave when being incident to an interface again may not be reverse to a phase of the ultrasonic waves U0. In contrast, in the present embodiment, interface reflected waves are reflected along the Z direction which is a normal direction to the interfaces F1 and F2 regardless of a reflection position, and thus it is possible to prevent the occurrence of the problem, and to more reliably cancel out the interface reflected waves.

In the present embodiment, the piezoelectric element 413 is provided on the operation surface 412B side of the vibration film 412, and an ultrasonic wave is transmitted from the ultrasonic wave transmission/reception surface 412A. In this configuration, for example, compared with a configuration in which the piezoelectric element 413 is provided on the ultrasonic wave transmission/reception surface 412A side, it is possible to improve the flatness of the ultrasonic wave transmission/reception surface 412A which is an interface between the acoustic matching layer 43 and the ultrasonic transducer 45. Therefore, it is possible to make distances between the ultrasonic wave transmission/reception surface 412A and the respective interfaces F1 and F2 more uniform, and thus to more reliably cancel out interface reflected waves.

In the present embodiment, the first layer 431 of the acoustic matching layer 43 fills the opening 411A formed in the board main body portion 411. In this configuration, it is possible to form the first layer 431 according to a depth of the opening 411A. It is possible to adjust a thickness of the first layer 431 to an appropriate value by adjusting a thickness of the opening 411A as appropriate, and thus to easily form the first layer 431 having a desired thickness.

In the present embodiment, the adjustment member 417 adjusting a thickness of the second layer 432 of the acoustic matching layer 43 is provided. The adjustment member 417 is a frame-shaped member disposed on the board main body portion 411 on the +Z side. It is possible to form the second layer 432 according to a thickness of the adjustment member 417 by forming the second layer 432 in the recess surrounded by the adjustment member 417. Therefore, it is possible to adjust a thickness of the second layer 432 to an appropriate value by adjusting a thickness of the adjustment member 417 as appropriate, and thus to easily form the second layer 432 having a desired thickness.

Second Embodiment

Next, an ultrasonic device according to a second embodiment will be described.

In the first embodiment, a description has been made of an exemplary configuration in which the ultrasonic device 22 includes the acoustic matching layer 43 formed of the first layer 431 and the second layer 432. In contrast, an ultrasonic device of the second embodiment is different from the ultrasonic device of the first embodiment in that an acoustic matching layer 47 is provided instead of the acoustic matching layer 43.

Figure 12:
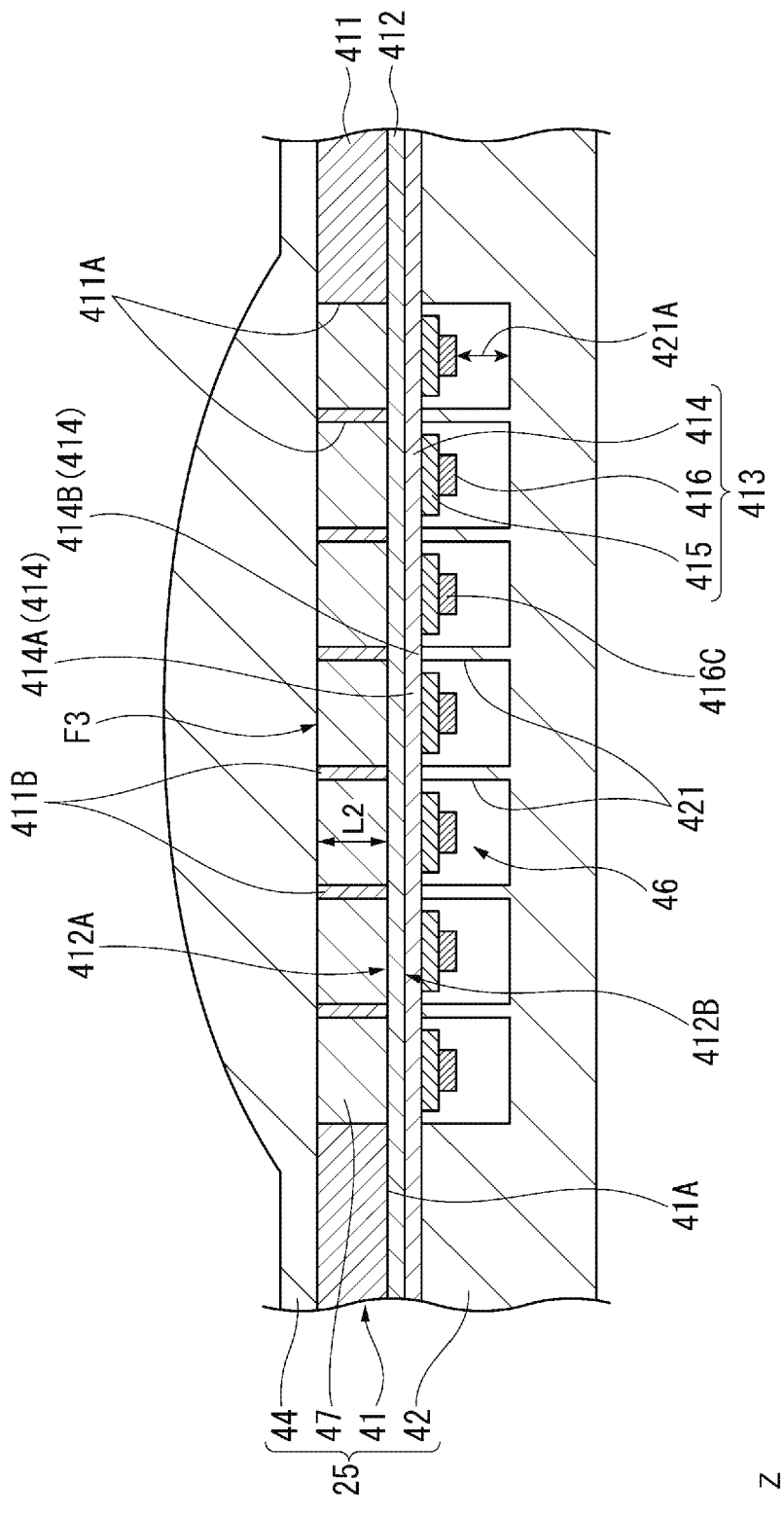
FIG. 12 is a sectional view illustrating a schematic configuration of an ultrasonic device according to a second embodiment.

FIG. 12 is a sectional view schematically illustrating a section of an ultrasonic device 25 of the second embodiment.

As illustrated in FIG. 12, the ultrasonic device 25 is formed of an element board 41, a sealing plate 42, an acoustic matching layer 47, and an acoustic lens 44.

The element board 41 of the present embodiment is configured substantially in the same manner as in the first embodiment except that a depth dimension of the opening 411A is an integer multiple of $\lambda/2$ when a wavelength of an ultrasonic wave transmitted from the ultrasonic transducer 45 is indicated by $\lambda$.

The acoustic matching layer 47 is made of a material having acoustic impedance lower than that of the acoustic lens 44 in the same manner as in the second layer 432 of the first embodiment. The acoustic matching layer 47 fills the opening 411A. The acoustic lens 44 is disposed on the +Z side of the acoustic matching layer 47.

A thickness dimension L2 of the acoustic matching layer 47, that is, a distance L2 from an interface F3 between the acoustic matching layer 47 and the acoustic lens 44 to the ultrasonic wave transmission/reception surface 412A satisfies the following Equation (2) when a wavelength of an ultrasonic wave transmitted from the ultrasonic transducer 45 is indicated by $\lambda$, and n is an integer of 1 or more. In other words, the acoustic matching layer 47 is formed so that the dimension L2 is an integer multiple of $\lambda/2$. Also in the present embodiment, it is possible to adjust a thickness of the acoustic matching layer 47 according to a depth of the opening 411A.

$$L2=(\lambda/2)\times n \qquad (2)$$

Prevention of Tailing Using Acoustic Matching Layer

Also in the present embodiment, it is possible to prevent the occurrence of tailing caused by interface reflected waves generated at the interface F3 and thus to improve a distance resolution. In other words, a phase of interface reflected waves which are generated at the interface F3 and propagate in the −Z direction is inverted when being reflected at the ultrasonic wave transmission/reception surface 412A. Thus, if a thickness (a distance between the ultrasonic wave transmission/reception surface 412A and the interface F3) of the acoustic matching layer 47 is set to an integer multiple of $\lambda/2$, a phase of interface reflected waves when being incident to the interface F3 again can be made reverse to a phase of the ultrasonic waves U0 (refer to FIG. 5) transmitted from the ultrasonic transducer 45. As mentioned above, at least some interface reflected waves, which are reflected at the interface F3 so as to be reflected at the ultrasonic wave transmission/reception surface 412A, and are then incident to the interface F3 again, are canceled out by the ultrasonic waves U0. Therefore, it is possible to prevent the interface reflected waves from being emitted to a living body later than the ultrasonic waves U0, and thus to improve a distance resolution.

Figure 13:
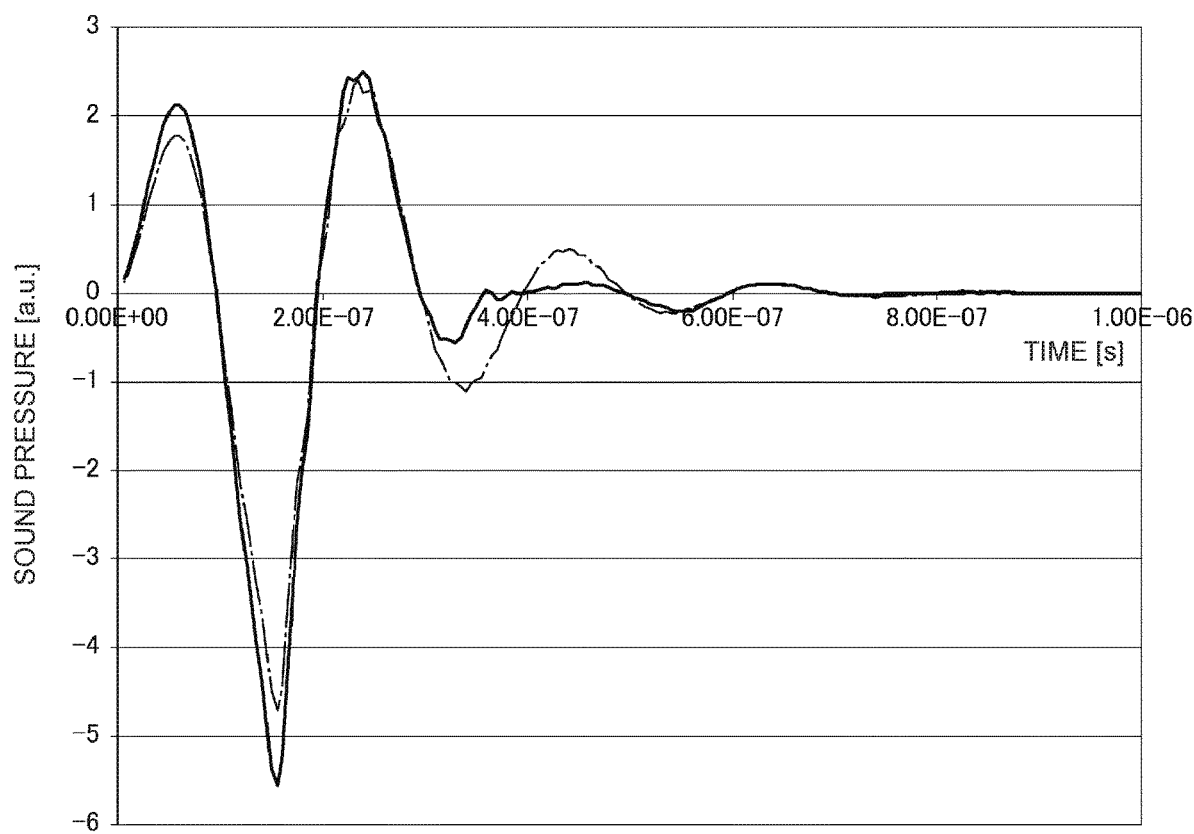
FIG. 13 is a diagram illustrating changes in sound pressure due to ultrasonic waves transmitted from the ultrasonic device according to the second embodiment and an ultrasonic device according to a comparative example.

FIG. 13 is a diagram illustrating an example of a temporal change of an ultrasonic wave transmitted from the ultrasonic device 25. In the same manner as in FIG. 6, in FIG. 13, a temporal change of an ultrasonic wave emitted from the ultrasonic device 25 of the present embodiment is indicated by a solid line. On the other hand, a dot chain line illustrates an example of a temporal change of an ultrasonic wave transmitted from an ultrasonic device according to a comparative example, further including an acoustic matching layer whose thickness is not an integer multiple of $\lambda/2$. In FIG. 13, a value of acoustic impedances of the acoustic lens 44 is 1.5 MRayls, a value of acoustic impedance of the acoustic matching layer 47 is 1 MRayls, and a Q value of the ultrasonic device 25 is 2. For example, a drive voltage having a waveform of a burst wave with 5 MHz is applied to the ultrasonic transducer 45.

As illustrated in FIG. 13, in the ultrasonic device 25 of the present embodiment indicated by the solid line, it can be seen that a change in sound pressure after about $3.00\times10^{-7}$ sec is reduced, and thus tailing is prevented, relative to the comparative example indicated by the dot chain line.

Operations and Effects of Second Embodiment

In the ultrasonic device 25 of the present embodiment, the acoustic matching layer 47 is formed of a single layer, and has a thickness corresponding to an integer multiple of $\lambda/2$ with a wavelength of an ultrasonic wave as $\lambda$. The acoustic impedance of the acoustic matching layer 47 is lower than that of the acoustic lens 44. In the ultrasonic device 25 having the above-described configuration, even if interface reflected waves are generated at the interface F3 between the acoustic matching layer 47 and the acoustic lens 44, a phase of the interface reflected waves can be made reverse to a phase of the ultrasonic waves U0 transmitted from the ultrasonic transducer 45 as described above when the interface reflected waves are incident to the interfaces F3 again. Therefore, at least some of the interface reflected waves are canceled out, and thus it is possible to prevent the interface reflected waves from being emitted to a measurement target from the acoustic lens 44 later than the ultrasonic waves U0, and thus to improve a distance resolution.

Third Embodiment

Next, an ultrasonic device according to a third embodiment will be described.

In the second embodiment, a description has been made of an exemplary configuration in which the ultrasonic device 25 includes the acoustic lens 44 provided on the acoustic matching layer 47. In contrast, an ultrasonic device of the third embodiment is different from the ultrasonic device of the second embodiment in that an intermediate layer 48 is provided between the acoustic matching layer 47 and the acoustic lens 44.

Figure 14:
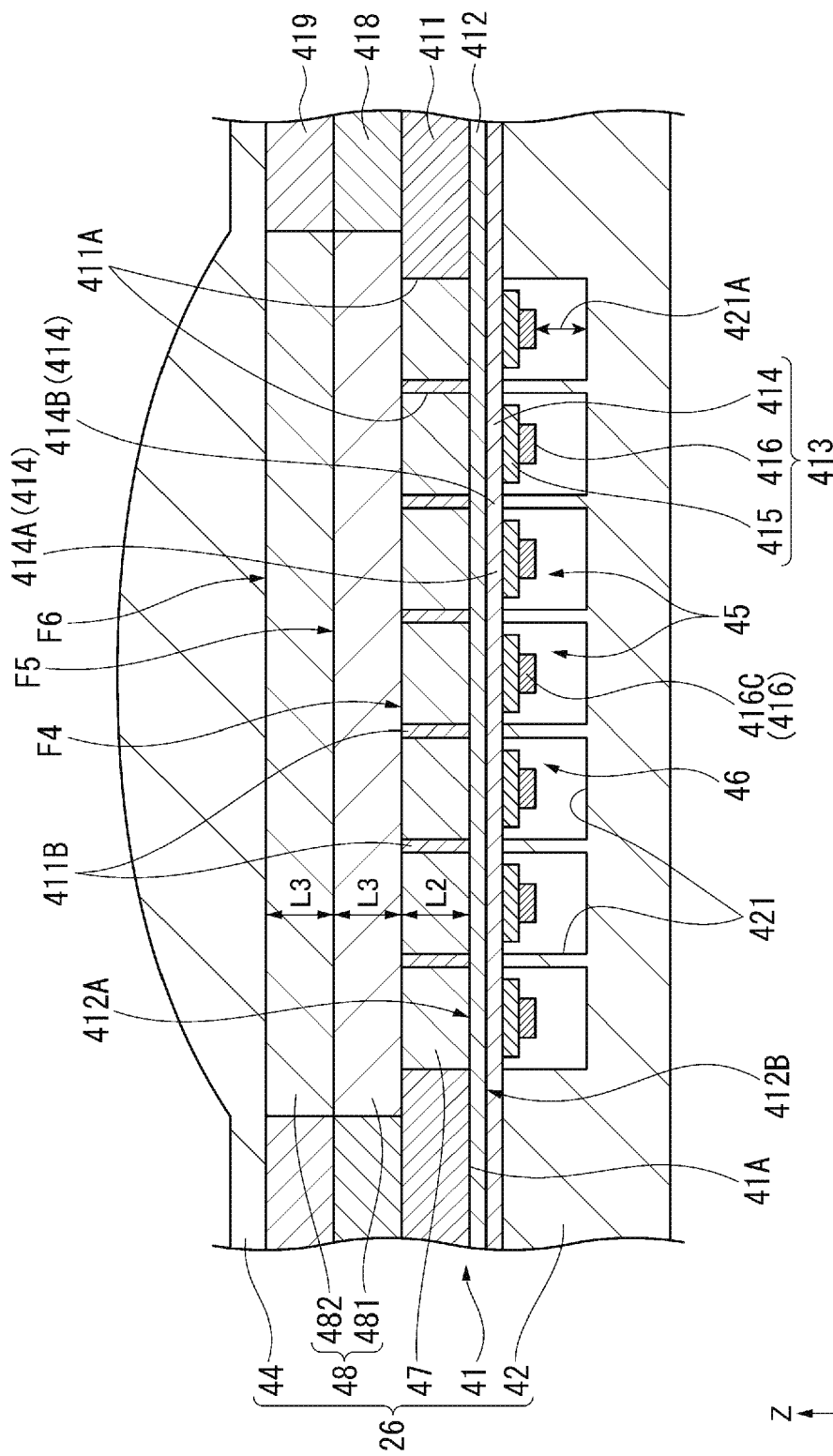
FIG. 14 is a sectional view illustrating a schematic configuration of an ultrasonic device according to a third embodiment.

FIG. 14 is a sectional view schematically illustrating a section of an ultrasonic device 26 according to the third embodiment.

As illustrated in FIG. 14, the ultrasonic device 26 is formed of an element board 41, a sealing plate 42, an acoustic matching layer 47, an intermediate layer 48, and an acoustic lens 44. The third embodiment is configured substantially in the same manner as the second embodiment except that the intermediate layer 48 includes a first intermediate layer 481 and a second intermediate layer 482, and a first adjustment member 418 adjusting a thickness of the first intermediate layer 481 and a second adjustment member 419 adjusting a thickness of the second intermediate layer 482 are provided.

The first adjustment member 418 is formed in the same manner as the adjustment member 417 of the first embodiment, and is provided on the +Z side of the board main body portion 411. A recess surrounded by the first adjustment member 418 is filled with the first intermediate layer 481 of the intermediate layer 48. Therefore, it is possible to adjust a thickness of the first intermediate layer 481 by adjusting a thickness of the first adjustment member 418 as appropriate.

The second adjustment member 419 is provided on the +Z side of the first adjustment member 418. A recess surrounded by the second adjustment member 419 is filled with the second intermediate layer 482. Therefore, it is possible to adjust a thickness of the second intermediate layer 482 by adjusting a thickness of the second adjustment member 419 as appropriate.

The acoustic lens 44 is disposed on the +Z side of the second adjustment member 419 and the second intermediate layer 482.

As illustrated in FIG. 14, the intermediate layer 48 includes the first intermediate layer 481 provided on the acoustic matching layer 47, and the second intermediate layer 482 provided on the first intermediate layer 481. Of the layers, the first intermediate layer 481 corresponds to the first layer 431 of the first embodiment, and the second intermediate layer 482 corresponds to the second layer 432 of the first embodiment. In other words, the acoustic impedance of the first intermediate layer 481 is higher than the acoustic impedance of the second intermediate layer 482, and is higher than the acoustic impedance of the acoustic matching layer 47. The acoustic impedance of the second intermediate layer 482 is lower than the acoustic impedance of the acoustic lens 44.

An interface (hereinafter, also (referred to as a first interface F4) between the acoustic matching layer 47 and the first intermediate layer 481, an interface (hereinafter, also referred to as a second interface F5) between the first intermediate layer 481 and the second intermediate layer 482, and an interface (hereinafter, also referred to as a third interface F6) between the second intermediate layer 482 and the acoustic lens 44 are substantially parallel to the ultrasonic wave transmission/reception surface 412A.

The thickness dimension L3 (that is, a distance between the first interface F4 and the second interface F5 and a distance between the second interface F5 and the third interface F6) of each of the first intermediate layer 481 and the second intermediate layer 482 satisfies the following Equation (3) when a wavelength of an ultrasonic wave transmitted from the ultrasonic transducer 45 is indicated by $\lambda$, and n is an integer of 1 or more.

$$L3=(\lambda/4)\times(2n-1) \quad (3)$$

The intermediate layer 48 having the above-described configuration functions in the same manner as the acoustic matching layer 43 of the first embodiment. In other words, the first interface F4, the second interface F5, and the third interface F6 according to the invention respectively correspond to the ultrasonic wave transmission/reception surface 412A, the first interface F1, and the second interface F2 of the first embodiment.

The first interface F4 of the present embodiment corresponds to the interface F3 of the second embodiment.

Therefore, also in the ultrasonic device 26 configured as described above, in the same manner as in the first embodiment and the second embodiment, even if interface reflected waves are generated at the interfaces F4, F5 and F6, it is possible to prevent the occurrence of tailing caused by the interface reflected waves and thus to improve a distance resolution.

Operations and Effects of Third Embodiment

The ultrasonic device 26 of the present embodiment includes the acoustic matching layer 47 provided on the ultrasonic wave transmission/reception surface 412A of the vibration film 412, the intermediate layer 48 provided on the acoustic matching layer 47, and the acoustic lens 44 provided on the intermediate layer 48. The intermediate layer 48 includes the first intermediate layer 481 on the acoustic matching layer 47 side and the second intermediate layer 482 on the acoustic lens 44 side, and each layer has a thickness corresponding to an odd-numbered multiple of $\lambda/4$ with a wavelength of an ultrasonic wave as $\lambda$. The acoustic impedance of the second intermediate layer 482 is lower than the acoustic impedance of each of the first intermediate layer 481 and the acoustic lens 44. In the ultrasonic device 26 configured as mentioned above, even if interface reflected waves are generated at the respective interfaces F4, F5 and F6 of the acoustic matching layer 47, the intermediate layer 48 and the acoustic lens 44, a phase of the interface reflected waves can be made reverse to a phase of the ultrasonic waves U0 transmitted from the ultrasonic transducer 45 as described above when the interface reflected waves are incident to the interfaces again. Therefore, at least some of the interface reflected waves are canceled out, and thus it is possible to prevent the interface reflected waves from being emitted to a measurement target from the acoustic lens 44 later than the ultrasonic waves U0, and thus to improve a distance resolution.

In the present embodiment, the intermediate layer 48 is formed of two layers. Here, even in a configuration in which the intermediate layer 48 has even-numbered layers of four or more layers, and the first intermediate layer 481 and the second intermediate layer 482 are alternately disposed, it is possible to prevent the occurrence of tailing caused by interface reflected waves in the same manner. On the other hand, if the intermediate layer 48 is thick, attenuation of an ultrasonic wave increases, and thus there is concern that a transmission output of the ultrasonic wave, and further reception sensitivity may be reduced. The entire intermediate layer 48 may be thin by making each layer thin, but there is the limitation in making each layer thin. In contrast, the intermediate layer 48 is formed of two layers, and thus thinning is easily realized by thinning the intermediate layer 48.

Modification Examples

Each of the above-described embodiments is not limited to the configuration described in the embodiments, and modifications, alterations, and combinations of the respective embodiments may occur.

For example, in the first embodiment, a description has been made of an exemplary case where the acoustic matching layer 43 is formed of two layers, but this is only an example, and the acoustic matching layer 43 may be formed of even-numbered layers of four or more layers. In this case, there may be a configuration in which the first layer 431 and the second layer 432 are alternately disposed.

In the third embodiment, a description has been made of an exemplary case where the intermediate layer 48 is formed of two layers, but this is only an example, and the intermediate layer 48 may be formed of even-numbered layers of four or more layers. In this case, there may be a configuration in which the first intermediate layer 481 and the second intermediate layer 482 are alternately disposed.

In the first embodiment, a description has been made of an exemplary configuration in which the first layer 431 and the second layer 432 have the same thickness, but this is only an example, and the first layer 431 and the second layer 432 may have different thicknesses. Similarly, in the third embodiment, a description has been made of an exemplary configuration in which the first intermediate layer 481 and the second intermediate layer 482 have the same thickness, but this is only an example, and the first intermediate layer 481 and the second intermediate layer 482 may have different thicknesses.

In the first embodiment, a description has been made of an exemplary configuration in which the adjustment member 417 adjusting a thickness of the second layer 432 is provided on the element board 41, but the adjustment member 417 may be integrally formed with the element board 41, and the adjustment member 417 may not be provided. For example, a recess as an adjustment portion adjusting a thickness of the second layer 432 may be provided in the acoustic lens 44. Also in this case, it is possible to adjust a thickness of the second layer 432 by adjusting a depth of the recess of the acoustic lens 44.

The adjustment member 417 may not be provided. For example, a thickness may be adjusted after the second layer 432 is formed on the first layer 431, and the second layer 432 formed to have an appropriate thickness may be formed on the first layer 431.

In the same manner as in the third embodiment, a description has been made of an exemplary configuration in which the adjustment members 418 and 419 are provided on the element board 41, but this is only an example, and the adjustment members 418 and 419 may be integrally formed with the element board 41, and the adjustment members 418 and 419 may not be provided.

In the first embodiment, a description has been made of an exemplary configuration in which a thickness of the first layer 431 is the same as a depth of the opening 411A, and a thickness of the first layer 431 is adjusted depending on a depth of the opening 411A, but any other configuration may be used. For example, a depth of the opening 411A may be different from a thickness of the first layer 431. Similarly, in the second embodiment and the third embodiment, a thickness of the acoustic matching layer 47 may be different from a depth of the opening 411A.

In the above-described respective embodiments, as illustrated in FIG. 4, a description has been made of an exemplary configuration in which the board main body portion 411 provided with the opening 411A is provided on the ultrasonic wave transmission/reception surface 412A side of the vibration film 412, the piezoelectric element 413 is provided on the operation surface 412B side of the vibration film 412, and an ultrasonic wave is transmitted from and received by the ultrasonic wave transmission/reception surface 412A side, but any other configuration may be used.

For example, there may be a configuration in which the board main body portion 411 is provided on the ultrasonic wave transmission/reception surface 412A side of the vibration film 412, and the piezoelectric element 413 is provided on the ultrasonic wave transmission/reception surface 412A side. There may be a configuration in which the board main body portion 411 is provided on the operation surface 412B side of the vibration film 412, and the piezoelectric element 413 is provided on the ultrasonic wave transmission/reception surface 412A side. There may be a configuration in which the board main body portion 411 is provided on the operation surface 412B side of the vibration film 412, and the piezoelectric element 413 is provided in the opening 411A on the operation surface 412B side.

In the above-described respective embodiments, a description has been made of an exemplary configuration in which the piezoelectric element 413 of the ultrasonic transducer 45 is formed of a laminate in which the lower electrode 414, the piezoelectric film 415, and the upper electrode 416 are laminated in the thickness direction, but any other configuration may be used. For example, there may be a configuration in which a pair of electrodes are disposed to oppose each other on one surface side which is orthogonal to the thickness direction of the piezoelectric film 415. The electrodes may be disposed with the piezoelectric film interposed therebetween on a side surface along the thickness direction of the piezoelectric film.

In the above-described respective embodiments, a description has been made of an exemplary configuration in which the ultrasonic transducer 45 performs transmission and reception, but the ultrasonic transducer 45 may perform only transmission.

In the embodiments, a description has been made of an exemplary configuration in which the ultrasonic measurement apparatus employs a living body as a measurement target, but the invention is not limited thereto. For example, the invention is applicable to an electronic apparatus which employs various structural bodies as measurement targets, and detects defects of the structural bodies or examines deterioration thereof. For example, the invention is applicable to an electronic apparatus which employs various semiconductor packages, wafers, or the like as measurement targets, and detects defects of the measurement targets.

A specific structure at the time of implementing the invention may be configured by combining the respective embodiments and modification examples with each other as appropriate within the scope of being capable of achieving the object of the invention, and may be altered to other structures as appropriate.

The entire disclosure of Japanese Patent Application No. 2016-045884, filed on Mar. 9, 2016 is expressly incorporated by reference herein.

What is claimed is:

1. An ultrasonic device comprising:
   an ultrasonic transducer that has a vibration film and transmits an ultrasonic wave from a first surface of the vibration film;
   an acoustic matching layer that is provided on the first surface of the vibration film; and
   an acoustic lens that is provided on the acoustic matching layer, the acoustic matching layer being located closer to the vibration film than the acoustic lens,
   wherein the acoustic matching layer is formed of even-numbered layers including a first layer and a second layer, the second layer having acoustic impedance lower than acoustic impedance of each of the first layer and the acoustic lens, and the first layer and the second layer are disposed in this order toward the acoustic lens from the vibration film,
   wherein each of the first layer and the second layer has a thickness corresponding to an odd-numbered multiple of $\lambda/4$ with a wavelength of the ultrasonic wave as $\lambda$, and
   wherein an acoustic impedance difference between the first layer and the second layer is in a range of 0.1 MRayls to 1.0 MRayls.

2. The ultrasonic device according to claim 1,
   wherein the acoustic matching layer is formed of only a single layer of the first layer and a single layer of the second layer.

3. The ultrasonic device according to claim 1,
   wherein the first surface of the vibration film is planar, and
   wherein a surface of the acoustic matching layer facing the vibration film, a surface of the acoustic matching layer facing the acoustic lens, and a surface of the acoustic lens facing the acoustic matching layer are parallel to the first surface of the vibration film.

4. The ultrasonic device according to claim 1,
wherein the ultrasonic transducer includes a piezoelectric element provided on a second surface of the vibration film, and the second surface is opposite to the first surface.

5. The ultrasonic device according to claim 1,
wherein the ultrasonic transducer includes a substrate supporting the vibration film,
wherein the substrate includes a through hole having first and second openings opposite to each other, the first opening is closed by the vibration film, and the second opening is open, and
wherein at least a part of the acoustic matching layer is disposed inside the through hole.

6. The ultrasonic device according to claim 5, further comprising:
an adjustment member that is disposed on the substrate and adjusts a thickness of the acoustic matching layer,
wherein the substrate is located closer to the adjustment member than the acoustic lens.

7. The ultrasonic device according to claim 1,
wherein the acoustic impedance difference between the first layer and the second layer is in a range of 0.3 MRayls to 0.7 MRayls.

* * * * *